United States Patent
Pugin et al.

(10) Patent No.: US 6,515,183 B2
(45) Date of Patent: Feb. 4, 2003

(54) CHIRAL DIPHENYLDIPHOSPHINES AND D-8 METAL COMPLEXES THEREOF

(75) Inventors: Benoît Pugin, Muenchenstein (CH); Ivo Steiner, Lucerne (CH); Rhony Niklaus Aufdenblatten, Zermatt (CH); Antonio Togni, Russikon (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 09/899,205

(22) Filed: Jul. 6, 2001

(65) Prior Publication Data

US 2001/0056210 A1 Dec. 27, 2001

Related U.S. Application Data

(62) Division of application No. 09/441,519, filed on Nov. 17, 1999, now Pat. No. 6,281,390.

(30) Foreign Application Priority Data

Nov. 19, 1998 (CH) ............................................. 2319/98

(51) Int. Cl.$^7$ ................................................. C07F 9/50
(52) U.S. Cl. ........................ 568/12; 549/218; 556/404; 568/17
(58) Field of Search ............................ 556/404; 568/13, 568/15, 16, 17; 549/218; 562/9, 12

(56) References Cited

U.S. PATENT DOCUMENTS

| | | |
|---|---|---|
| 4,556,740 A | 12/1985 | Hansen et al. |
| 5,516,944 A | 5/1996 | Broger et al. |
| 5,852,212 A | 12/1998 | Broger et al. |
| 5,872,273 A | 2/1999 | Saito et al. |

FOREIGN PATENT DOCUMENTS

| | | |
|---|---|---|
| EP | 0104375 | 4/1984 |
| WO | 93/15090 | 8/1993 |
| WO | 98/01457 | 1/1998 |
| WO | 98/12202 | 3/1998 |

OTHER PUBLICATIONS

CA:134:266437 abs of WO 2001021625 Mar. 2001.*
CA:119:271398 abs of WO9315090 Aug. 1993.*
Robert E. Carter, et al., "N.m.r. Studies of a Rate Process in a Bridged Biphenyl: Resolution of a Discrepancy between N.m.r. and Polarimetric Kinetic Data", Organic Magnetic Resonance vol. 9, No. 1, 1997, pp. 44–48.

Rudolf Schmid, et al., "Axially Dissymmetric Bis(triaryl)phosphines in the Biphenyl Series: Synthesis of (6,6+40–Dimethylbiphenyl–2,2'–diyl)bis(diphenylphosphine) ('BIPHEMP') and Analogues, and their Use in Rh(I)–Catalyzed Asymmetric Isomerizations of N,N–Diethylnerylamine", Helvetica Chimica Acta, vol. 71 (4) (1988), pp. 897–929.

Francis A. McGinn, et al. "Direct Configurational Intercorrelation of 6,6'–Dinitro, 6,6'–Dichloro– and 6,6'–Dimethyl–2,2'–diphenic Acid. Absolute Configuration of 6,6'–Dimethyl–2,2'–biphenyldiamine$^1$", Journal of The American Chemical Society, vol. 80, No. 2, 1958, pp. 476–480.

Rudolf Schmid, et al. "New developments in enantioselective hydrogenation", Pure & Appl. Chem., vol. 68, No. 1, pp. 131–138, 1996.

* cited by examiner

Primary Examiner—Jean F. Vollano
(74) Attorney, Agent, or Firm—Wenderoth, Lind & Ponack, L.L.P.

(57) ABSTRACT

Compounds of formula III,

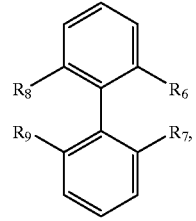

(III)

wherein $R_6$ und $R_7$ signify identical or different secondary phosphino; $R_8$ is —$CH_2$—OH, —$CH_2$—$NH_2$, —$CH_2$—O—B—FU, —$CH_2$—$NH_2$—B—FU, or —O—B—FU; $R_9$ has the same significance as $R_8$ or is $C_1$-$C_4$-alkyl or $C_1$-$C_4$-alkoxy; or $R_8$ and $R_9$ together signify HOCH($CH_2$—O—)$_2$, $H_2$NCH—($CH_2$—O—)$_2$, FU—B—OCH($CH_2$—O—)$_2$ or FU-B-HNCH($CH_2$—O—)$_2$; B is a bridging group; and FU is a functional group. The compounds may be bonded to inorganic or organic carriers. Their d-8 metal complexes are valuable catalysts for the enantioselective hydrogenation of prochiral organic compounds with carbon multiple bonds or carbon/hetero atom multiple bonds.

10 Claims, No Drawings

CHIRAL DIPHENYLDIPHOSPHINES AND D-8 METAL COMPLEXES THEREOF

This application is a divisional application of Ser. No. 09/441,519 filed Nov. 17, 1999, now U.S. Pat. No. 6,281,390.

The present invention relates to mono- and di-(halogenmethyl)-diphenyldiiodides, -dibromides and -diamines; mono- and di-(hydroxymethyl)-diphenyldiiodides, -dibromides and -diamines and mono- and di-(aminomethyl)-diphenyldiiodides, -dibromides and -diamines; mono- and di-(hydroxymethyl)-diphenyldiphosphines and mono- and di-(aminomethyl)-diphenyldiphosphines, as well as 2-hydroxypropane-1,3-dioxyl-diphenyldiphosphines; mono- and di-(hydroxymethyl)-diphenyldiphosphines and mono- and di-(aminomethyl)-di-phenyldiphosphines, as well as 2-hydroxypropane-1,3-dioxyl-diphenyldiphosphines, the hydroxyl groups or amino groups of which are provided with functional groups via a bridging group; inorganic and organic polymeric carriers which are immobilised with said diphosphines; metal complexes of the monomeric and immobilised diphosphines; and the use of the metal complexes as homogeneous and enantioselective catalysts in the synthesis of organic compounds, for example hydrogenation.

In Pure and Appl. Chem., Vol. 68, No. 1, pp. 131–138 (1996), R. Schmid et al. describe atropisomeric 6,6'-dimethyl- and 6,6'-dimethoxy-2,2'-diphenyldiphosphines as chiral ligands in metal complexes, which are used for the hydrogenation of prochiral ketones and olefins, whereby high optical yields may be attained. The catalysts can only be extracted from the reaction mixtures with difficulty and incompletely, so that it is impossible to reuse them for further reactions.

In WO 98/01457, B. Pugin et al. describe the functionalisation of chiral ferrocenyl-diphosphines as ligands for metal complexes and the immobilisation on inorganic and organic carriers, which may be used as enantioselective hydrogenation catalysts. These catalysts may be easily separated from the reaction mixture and reused.

It has now been found that, in a simple manner, functionalised 2,2'-diphenyldiphosphines can be prepared and may be immobilised both on inorganic and on organic polymeric carriers, and can also be used as water-soluble and/or extractable and/or adsorbable ligands/catalysts. The immobilised diphosphine ligands bond with d-8 metals such as rhodium, ruthenium and iridium complexes which may be used as highly effective catalysts in enantioselective hydrogenation of carbon-carbon, carbon-nitrogen or carbon-oxygen double bonds. The selectivity, activity and total yield for immobilised systems are surprisingly high.

The catalysts may be easily separated from the reaction solution and reused. Almost no metal or ligand losses occur. In addition, immobilised diphenyldiphosphine ligands especially on inorganic carriers have surprisingly high stability, which is especially important for reusage. Therefore, using these immobilised catalysts, large-scale hydrogenation may be carried out especially economically.

The reaction to be catalysed may be carried out even heterogeneously or homogeneously through the choice of polymer, for example in the case of polymer-bound diphosphine ligands. The polymer may be prepared in such a way, or also subsequently specifically modified in such a way that the polymer-bound catalyst dissolves in the reaction medium, and can be easily separated after the reaction by filtration, ultrafiltration, extraction or adsorption on carriers, and then reused. The catalysts can be reused several times. Through the choice of polymer, the catalyst may be optimally adapted to the reaction medium during the hydrogenation step, and then completely separated, which is important in particular for hydrogenation carried out on a large scale.

The production of these immobilised or extractable and/or adsorbable diphenyldiphosphines is made possible only by providing correspondingly functionalised diphenyldiphosphines. Therefore, particular importance is placed on these intermediates and their preparation.

In all cases, recovery of the noble metals contained therein is simplified if the catalyst has to be exchanged after frequent recycling. Frequently, further purification of the hydrogenated product can be dispensed with, since the catalyst can be removed practically quantitatively.

A first object of the invention is compounds of formula 1,

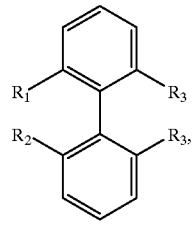

(I)

wherein
$R_1$ is methyl chloride, methyl bromide or methyl iodide, $R_2$ is $C_1$–$C_4$-alkyl or $C_1$–$C_4$-alkoxy or has the same significance as $R_1$, and $R_3$ is Br, I or —$NH_2$.

$R_1$ is preferably methyl bromide. $R_2$ is preferably alkyl, and as alkyl preferably signifies ethyl and most preferably methyl. $R_2$ as alkoxy preferably signifies methoxy or ethoxy. $R_3$ is preferably Br or I.

The preparation thereof may be effected in known manner by the radical halogenation of the methyl groups of 2,2'-di-$R_3$-6,6'-dimethyl-diphenyl with appropriate halogenation agents, for example $Cl_2$, $Br_2$, $I_2$, interhalogen compounds such as ClBr, ClI, or $SOCl_2$, $SOBr_2$, $SOI_2$, and organic halogen compounds such as $CF_3CL$, $CF_3Br$, $CF_3I$, $CCl_3I$, as well as N-halogenated acid amides, for example N-chloro-, -bromo- and -iodosuccinimide. Depending on the amount of halogenation agent, mono- or dihalogen-methyl-diphenyls are primarily obtained, whereby mixtures of the compounds may be separated by distillation, by chromatographic methods or by crystallisation. The oily or crystalline compounds of formula I are valuable initial products for the production of atropisomeric diphosphines.

A further object of the invention is compounds of formula II,

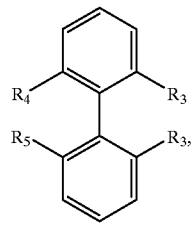

(II)

wherein
$R_3$ is Br, I or —$NH_2$, $R_4$ is hydroxymethyl, aminomethyl, hydroxy-, amino- or cyano-$C_2$–$C_8$-alkoxy, hydroxy-, amino- or cyano-$C_2$–$C_8$-alkoxymethyl, or hydroxy-, amino- or cyano-$C_2$–$C_8$-alkylaminomethyl, and $R_5$ has the same significance as $R_4$, or $R_5$ is $C_1$–$C_4$-alkyl or $C_1$–$C_4$-alkoxy, or $R_4$ and $R_5$ together are $HOCH(CH_2$—$O$—$)_2$, $H_2NCH(CH_2$—$O$—$)_2$, or hydroxy-, amino- or cyano-$C_2$–$C_8$-alkylOCH($CH_2$—$O$—$)_2$.

$R_3$ is preferably Br or I and especially I. $C_2$–$C_8$-alkyl in the hydroxy-, amino- or cyanoalkyl groups is preferably $C_2$–$C_6$-alkyl, more preferably $C_2$–$C_4$-alkyl, for example $C_2$-, $C_3$-alkyl or $C_4$-alkyl. $R_5$ as $C_1$–$C_4$-alkyl or $C_1$–$C_4$-alkoxy may be for example methyl, ethyl, propyl, butyl, methoxy, ethoxy, propyloxy and butyloxy; methyl and methoxy are preferred. If $R_5$ signifies alkyl, $R_4$ is preferably hydroxymethyl, aminomethyl, hydroxy-, amino- or cyano-$C_2$–$C_8$-alkoxymethyl, or hydroxy-, amino- or cyano-$C_2$–$C_8$-alkylaminomethyl If $R_5$ signifies alkoxy, $R_4$ is preferably amino- or cyano-$C_2$–$C_8$-alkoxy. The hydroxy, amino or cyano groups are preferably primary groups.

The compounds of formula II may be produced by known synthesis methods. Thus, the methyl halide group in the compounds of formula I can be hydroxylated or aminated in known manner. These hydroxy or amino compounds, or the known 2-alkoxy-2'-hydroxy-6,6'-substituted diphenyl, or the known 2,2'-dihydroxy-6,6'-substituted diphenyl, or a compound of formula

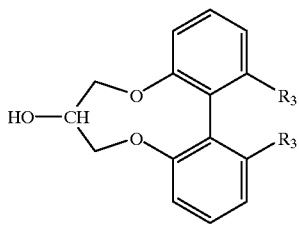

which is obtainable by reacting 2,2'-dihydroxy-6,6'-substituted diphenyl with epichlorohydrin or 1,3-dichloro-2-hydroxypropane, is reacted with cyanoalkenyl and then the cyano group is hydrogenated, or reacted with hydroxyhalogen- or aminohalogen-alkanes, or with ethylene oxide or aziridine. The HO group may be substituted by a $NH_2$ group in known manner, for example first of all halogenated and then reacted with 1,1'-carbonyl-diimidazole; hydrolysis then yields the free amine.

The compounds of formula II are eminently suitable for producing corresponding diphenyldiphosphines, in which the functional groups may undergo prior or subsequent modification in conventional manner by conversion into other functional groups or by a reaction with difunctional chain extenders, for example epoxides, hydroxyalkyl cyanates, halo-alkanols, halo-alkane nitrites, halo-alkane phthalimides, dicarboxylic acids or diisocyanates. The phosphine groups are introduced in known manner [see Pure and Appl. Chem., Vol. 68, No. 1, pp. 131–138 (1996)] by reacting compounds of formula II with lithium alkyls, for example lithium butyl, and reacting these with secondary phosphine halides, for example chlorides. The functional groups may be provided with appropriate protecting groups, a large number of which are known. The introduction of the phosphine groups may also take place in stages, whereupon unsymmetrically substituted diphenyldiphosphines are obtainable. This functionalisation is described in detail in WO 98/01457.

Further objects of the invention are also the compounds of formula III,

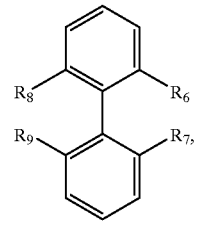

(III)

wherein
$R_6$ and $R_7$ signify identical or different secondary phosphino,
$R_8$ is —$CH_2$—OH, —$CH_2$—$NH_2$, —$CH_2$—O—B—(FU)$_p$, —$CH_2$—NR'—B—(FU)$_p$, or —O—B—(FU)$_p$,
$R_9$ has the same significance as $R_8$ or is $C_1$–$C_4$-alkyl or $C_1$–$C_4$-alkoxy, or
$R_8$ and $R_9$ together signify HOCH($CH_2$—O—)$_2$, $H_2$NCH($CH_2$—O—)$_2$, (FU)$_p$—B—OCH($CH_2$—O—)$_2$ or (FU)$_p$—B—R'NCH($CH_2$—O—)$_2$,
R' is H or $C_1$–$C_4$ alkyl;
B is a bridging group,
FU is a functional group,
p is a number from 1 to 6, and
$NH_2$ groups are present as such or as masked isocyanate groups.

In formula III, p is preferably a number from 1 to 4, most preferably 1 to 3. Preferred compounds having more than one functional group are those of formula IIIb

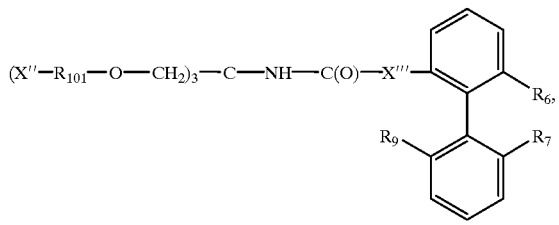

(IIIb)

wherein $R_6$ and $R_7$ are defined as above, $R_9$ is $C_1$–$C_4$-alkyl and preferably methyl, $R_{101}$ is $C_2$–$C_{12}$-, preferably $C_2$–$C_6$-, most preferably $C_2$ to $C_4$-alkylene, X" is —COOH and X'" is —O—, —NH— or —N($C_1$–$C_4$-alkyl), as well as the amides, esters and salts thereof, especially alkali or alkaline earth metal salts.

If $R_8$ and $R_9$ contain a primary amino group, this may be converted by known methods into masked isocyanate groups, which similarly represent valuable functional groups.

The secondary phosphino may correspond to formula —P$R_{10}R_{11}$, wherein $R_{10}$ and $R_{11}$, independently of one another, are $C_1$–$C_{12}$-alkyl, $C_5$–$C_{12}$-cycloalkyl; phenyl, $C_5$–$C_{12}$-cycloalkyl substituted by $C_1$–$C_4$-alkyl or $C_1$–$C_4$-alkoxy; or phenyl mono- to trisubstituted by $C_1$–$C_4$-alkyl, $C_1$–$C_4$-alkoxy, —Si$R_{12}R_{13}R_{14}$, halogen, —$SO_3$M, —$CO_2$M, —$PO_3$M, —$NR_{15}R_{16}$, —[$^+NR_{15}R_{16}R_{17}$]X$^-$ or $C_1$–$C_5$-fluoroalkyl; $R_{10}$ and $R_{11}$ together are tetra- or pentamethylene either unsubstituted or mono- to trisubstituted by $C_1$–$C_4$-alkyl, $C_1$–$C_4$-alkoxy, —Si$R_{12}R_{13}R_{14}$, halogen, —$SO_3$M, —$CO_2$M, —$PO_3$M, —$NR_{15}R_{16}$, —[$^+NR_{15}R_{16}R_{17}$]X$^-$ or $C_1$–$C_5$-fluoroalkyl, or the group —P$R_{10}R_{11}$ represents a radical of formulae

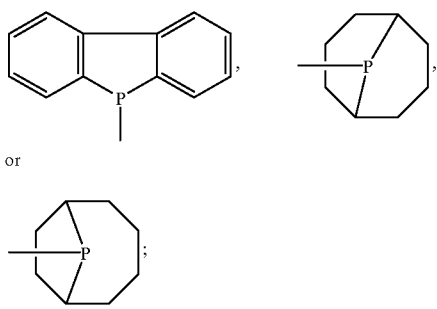

and $R_{12}$, $R_{13}$ and $R_{14}$ independently of one another, are $C_1$–$C_{12}$-alkyl or phenyl $R_{15}$ and $R_{16}$, independently of one another, are H, $C_1$–$C_{12}$-alkyl or phenyl, or $R_{15}$ and $R_{16}$ together are tetramethylene, pentamethylene or 3-oxa-1,5-pentylene;

$R_{17}$ is H or $C_1$–$C_4$-alkyl;

M is H or an alkali metal;

X is the anion of a monobasic acid;

halogen is fluorine, chlorine, bromine or iodine.

The alkyl and alkoxy substituents in question may be, for example, methyl, ethyl, n- and isopropyl, n-, iso- and tert.-butyl, methoxy, ethoxy, n- and isopropoxy, n-, iso- and tert.-butoxy.

$R_{10}$ and $R_{11}$ in the definition of alkyl may be linear or branched and they preferably contain 1 to 8, most preferably 1 to 4 carbon atoms. Examples of this alkyl are methyl, ethyl, n- and isopropyl, n-, iso- and tert.-butyl, pentyl, hexyl, heptyl, octyl, nonyl, decyl, undecyl and dodecyl. Preference is given to methyl, ethyl, n- and isopropyl, n-, iso- and tert.-butyl. If $R_{10}$ and $R_{11}$ are identical, then as alkyl they most preferably signify isopropyl or tert.-butyl.

$R_{10}$ and $R_{11}$ in the definition of cycloalkyl preferably contain 5 to 8, most preferably 5 or 6 ring carbon atoms. Examples of cycloalkyl are cyclopentyl, cyclohexyl, cycloheptyl, cyclooctyl, cyclodecyl and cyclododecyl. Preference is given to cyclopentyl and cyclohexyl, and especially cyclohexyl.

The cycloalkyl may be substituted, for example by 1 to 3 alkyl or alkoxy substituents; examples of such substituents have already been given. Preference is given to methyl and ethyl, as well as methoxy and ethoxy. Examples of substituted cycloalkyl are methyl- and methoxycyclopentyl and cyclohexyl.

$R_{10}$ and $R_{11}$ in the definition of substituted phenyl preferably contain 1 or 2 substituents. Where phenyl contains 2 or 3 substituents, these may be identical or different. Examples of alkyl and alkoxy substituents have already been given; preferred alkyl and alkoxy substituents for phenyl are methyl, ethyl and methoxy and ethoxy.

If the phenyl substituent is halogen, this is preferably —F, —Cl and —Br.

If the phenyl substituent is $C_1$–$C_5$-fluoroalkyl, this is partly or wholly fluorinated $C_1$–$C$-alkyl. Examples thereof are the position isomers of mono- to decafluoropentyl, mono- to octafluorobutyl, mono- to hexafluoropropyl, mono- to tetrafluoroethyl and mono- and difluoromethyl. Of the partly fluorinated alkyl radicals, those of formulae —$CF_2H$ and —$CF_2$($C_1$–$C_4$-alkyl) are preferred in particular. A perfluorinated alkyl is especially preferred. Examples thereof are perfluoropentyl, perfluorobutyl, perfluoropropyl, perfluoroethyl and in particular trifluoromethyl. The fluorine-substituted alkyl groups are preferably bonded in positions 3, 4 and 5.

$R_{12}$, $R_{13}$ und $R_{14}$ may be linear or branched alkyl, which preferably contains 1 to 8, most preferably 1 to 4 carbon atoms. Examples of alkyl have already been given. The preferred alkyl is methyl, ethyl, n-propyl, n-butyl and tert.-butyl. The substituent —$SiR_{12}R_{13}R_{14}$ is most preferably trimethylsilyl.

Of the acidic phenyl substituents —$SO_3M$, —$CO_2M$ and —$PO_3M$, the group —$SO_3M$ and —$CO_2M$ is preferred. M is preferably H, Li, Na and K.

$R_{16}$ and $R_{17}$ as alkyl preferably contain 1 to 6, most preferably 1 to 4 carbon atoms. The alkyl is preferably linear. Preferred examples are methyl, ethyl, n-propyl and n-butyl. $R_{18}$ as alkyl is preferably methyl.

$X^-$ as the anion of a monobasic acid is preferably $Cl^-$, $Br^-$ or the anion of a carboxylic acid or sulphonic acid, for example formate, acetate, trichloroacetate or trifluoroacetate. Preferred examples of $R_{10}$ and $R_{11}$ as substituted phenyl are 2-methyl-, 3-methyl-, 4-methyl-, 2- or 4-ethyl-, 2- or 4-isopropyl-, 2- or 4-tert.-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4—$SO_3H$—, 2- or 4—$SO_3Na$—, 2- or 4-[$^+NH_3Cl^-$]—, 3,4,5-trimethylphen-1-yl, 2,4,6-trimethylphen-1-yl, 4-trifluoromethyl-phenyl or 3,5-di-(trifluoromethyl)-phenyl.

Especially preferred examples of $R_{10}$ and $R_{11}$ are cyclohexyl, tert.-butyl, phenyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl, but most preferably cyclohexyl, phenyl, 4-methylphen-1-yl and tert.-butyl.

Another preferred group of compounds is obtained if $R_{10}$ and $R_{11}$ signify unsubstituted phenyl or mono- or disubstituted phenyl.

A further group of especially preferred compounds is obtained if $R_{10}$ and $R_{11}$ are identical and denote phenyl, cyclohexyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl; $R_{10}$ and $R_{11}$ are most preferably identical radicals and signify cyclohexyl or phenyl.

In the context of this invention, functional group means that this group forms a chemical bond by addition or substitution with other functional groups.

At the functional groups, chain lengthening may be undertaken for example and/or a polymerisable group may be bonded by known methods. Known methods are for example etherification, esterification, amidation, urea formation and urethane formation.

Processes for the derivatisation of functional groups are known from organic chemistry textbooks (E. Breitmaier, Günther Jung; Organische Chemie II (1983); Georg Thieme Verlag Stuttgart, New York pp.342, 409ff).

Examples of C-bonded functional groups are the carboxylic acid, carboxylate, carboxylic acid ester, carboxylic acid amide, carboxylic acid halide, cyano, imino, aldehyde, ketone, amine, alcohol, isocyanate, halogen or glycidyl group.

The functional group may also be a polymerisable group, and in this case is preferably a vinyl group that is unsubstituted or substituted by $C_1$–$C_4$-alkyl. It may be bonded, for example, by an amide or ester group to the bridging group.

The polymerisable group may be derived from ethylenically unsaturated alcohols, amines and isocyanates, for example allyl alcohol, allyl amine, allyl isocyanate, croton alcohol; monoesters or monoamides of dicarboxylic acids and unsaturated alcohols and amines; functional styrenes, for example chloromethylstyrene, hydroxystyrene, hydroxyethoxystyrene, styreneamine, styrenehydroxyethylamine, styrenecarboxylic acid, styrenesulphonic acid, vinyl hydroxyethylether, acrylic acid, methacrylic acid, acrylic and methacrylic acid amide, acrylic- and methacrylic acid-$C_2$–$C_6$-hydroxyalkyl-amide, acrylic- and methacrylic acid-$C_2$–$C_6$-hydroxyalkyl-ester.

The functional group which is bonded by a bridging group B to one of its carbon atoms preferably signifies an amine, alcohol, isocyanate, carboxylic acid, carboxylic acid ester, carboxylic acid amide, carboxylic acid halide group or a polymerisable group.

Linkage by means of these functional groups may be carried out by generally known processes. It is fundamentally also possible to transform existing functional groups into other functional groups, for example —$CH_2OH$ groups by oxidation into carboxylic acids, carboxylic acids into amides or halides, amine groups into isocyanate groups, alcohols or amines into carbonates or urethanes. Furthermore, it is possible to react alcohols or amines first of all with halocarboxylic acids (for example chloroacetic acid). Chain extenders, for example epoxides, aziridines, diols, diamines, dicarboxylic acids or dicarboxylic acid esters and diisocyanates, may also be used once or repeatedly in series, thus specifically determining the length of the extending group. These linking methods and processes are known and are described in specialist literature.

If the functional group FU signifies (O)C—H, (O)C—($C_1$–$C_{12}$)-alkyl, COOH, COCl or COO($C_1$–$C_6$)-alkyl, these groups can also be converted into other functional groups by reduction, transesterification or other known standard reactions from organic chemistry. For example, the aldehyde group is easily converted into an amine group by means of a reaction with an amine and subsequent hydrogenation. Reduction to the alcohol with, for example, $LiAlH_4$ is likewise possible.

If the functional group signifies OH, $NH_2$ or NH($C_1$–$C_{12}$-alkyl), it can be functionalised to an oxyalkylsilyl group by means of a reaction with a compound of formula $(R_{18})_n$ $(R_{19}O)_{3-n}$—Si—$R_{20}$—NCO, whereby $R_{20}$ is $C_1$–$C_{12}$-alkylene, $R_{19}$ is $C_1$–$C_{12}$ alkyl, $R_{18}$ is $C_1$–$C_{12}$alkyl or $OR_{19}$ and n is 0, 1 or 2.

The bridging group B may contain 1 to 30 atoms, preferably 1 to 20 atoms, and most preferably 1 to 12 atoms in the chain, selected from the group C, O, S and N. The bridging group in question is preferably hydrocarbon radicals, that may be interrupted by one or more hetero atoms from the group O, S and N and/or the group C(O).

The bridging group B may correspond to formula (IV)

wherein $X_1$ is a direct bond, or $X_1$ is selected from the group —C(O)—, —O—C(O)—, —$SO_2$—, —O—$SO_2$—, —$NR_{101}$—C(O)—, —$NR_{101}$—C(O)—, —$NR_{101}SO_2$— or —$NR_{101}$—$SO_2$—, wherein $R_{101}$ is H or $C_1$–$C_{30}$-alkyl, $C_5$- or $C_6$-cycloalkyl, $C_5$- or $C_6$-cycloalkylmethyl or -ethyl, phenyl, benzyl or 1-phenyleth-2-yl and $R_{100}$ is a bivalent bridging group.

$R_{101}$ defined as alkyl preferably contains 1 to 6, most preferably 1 to 4 carbon atoms. Some examples are methyl, ethyl, n- or isopropyl, butyl, hexyl and octyl. $R_{101}$ defined as cycloalkyl is preferably cyclohexyl, and defined as cycloalkylmethyl is cyclohexylmethyl. In a preferred embodiment, $R_{101}$ is H or $C_1$–$C_4$-alkyl.

The bivalent bridging group $R_{100}$ is preferably a hydrocarbon radical, which preferably contains 1 to 30, more preferably 1 to 18, most preferably 1 to 12, particularly preferably 1 to 8 carbon atoms, and is unsubstituted or mono- or polysubstituted by $C_1$–$C_4$-alkyl, $C_1$–$C_4$-alkoxy or =O. The hydrocarbon radical may also be interrupted once or many times by hetero atoms selected from the group —O—, —S— and —$NR_{101}$—, whereby $R_{101}$ is preferably H or $C_1$–$C_4$-alkyl.

The bivalent bridging groups $R_{100}$ may be for example $C_1$–$C_{20}$-, preferably $C_2$–$C_{12}$-alkyls, which can be linear or branched. Some examples are methylene, ethylene, 1,2- or 1,3-propylene, 1,2-, 1,3- or 1,4-butylene, pentylene, hexylene, octylene, dodecylene, tetradecylene, hexadecylene and octadecylene.

The bivalent bridging group $R_{100}$ may be for example polyoxaalkylene with 2 to 12, preferably 2 to 6, most preferably 2 to 4 oxyalkylene units and 2 to 4, preferably 2 or 3 carbon atoms in the alkylene. It is most preferably polyoxyethylene and polyoxypropylene with 2 to 6 oxyalkylene units.

The bivalent bridging group $R_{100}$ may be for example $C_5$–$C_{12}$-, preferably $C_5$–$C_8$-, most preferably $C_5$- or $C_6$-cycloalkyl, for example cyclopentylene, cyclohexylene, cyclooctylene or cyclododecylene.

The bivalent bridging group $R_{100}$ may be for example $C_5$–$C_{12}$-, preferably $C_5$–$C_8$-, most preferably $C_5$- or $C_6$-cycloalkyl-$C_1$–$C_{12}$- and preferably —$C_1$–$C_4$-alkyl. Some examples are cyclopentyl-$C_nH_{2n}$— and cyclohexyl-$C_nH_{2n}$—, wherein n is a number from 1 to 4. -Cyclohexyl-$CH_2$— is preferred in particular.

The bivalent bridging group $R_{100}$ may be for example $C_5$–$C_{12}$—, preferably $C_5$–$C_8$—, most preferably $C_5$- or $C_6$-cycloalkyl-($C_1$–$C_{12}$-alkyl)$_2$— and preferably (—$C_1$–$C_4$-alkyl)$_2$. Some examples are cyclopentyl-($C_nH_{2n}$—)$_2$ and cyclohexyl-($C_nH_{2n}$—)$_2$, wherein n is a number from 1 to 4. —$CH_2$-cyclohexyl-$CH_2$— is preferred in particular.

The bivalent bridging group $R_{100}$ may be for example $C_6$–$C_{14}$-arylene and preferably $C_6$–$C_{10}$-arylene, for example naphthylene or more preferably phenylene.

The bivalent bridging group $R_{100}$ may be for example $C_7$–$C_{20}$-aralkylene and preferably $C_7$–$C_{12}$-aralkylene More preferred is arylene-$C_nH_{2n}$—, wherein arylene is naphthylene and especially phenylene and n is a number from 1 to 4. Examples are benzylene and phenylethylene.

The bivalent bridging group $R_{100}$ may be for example arylene-($C_nH_{2n}$—)$_2$—, wherein arylene is preferably naphthylene and especially phenylene, and n is a number from 1 to 4. Examples are xylylene and phenylene($CH_2CH_2$)$_2$—.

A preferred group of compounds is formed if B signifies unsubstituted linear or branched $C_1$–$C_{12}$-alkylene, $C_2$–$C_{12}$-alkenylene, $C_2$–$C_{12}$-alkynylene, $C_5$–$C_{12}$-cycloalkylene, $C_5$–$C_{12}$-cycloalkenylene, phenylene, phenylene-($C_1$–$C_{12}$)-alkylene, or B signifies linear or branched $C_1$–$C_{12}$-alkylene, $C_2$–$C_{12}$-alkenylene, $C_2$–$C_{12}$-alkynylene, $C_5$–$C_{12}$-cycloalkylene, $C_5$–$C_{12}$-cycloalkenylene, phenylene or phenylene-($C_1$–$C_{12}$)-alkylene substituted by $C_1$–$C_4$-alkyl, $C_1$–$C_4$-alkoxy, halogen or hydroxy, and FU is halogen, OH, $NH_2$, NH($C_1$–$C_{12}$)-alkyl, (O)C—H, (O)C—($C_1$–$C_{12}$)-alkyl, COOH, COCl, COO($C_1$–$C_6$)-alkyl, —NCO or a group OC(O)—$CR_c$=$CR_dR_e$ or OC($NR_f$)—$CR_c$=$CR_dR_e$, wherein $R_c$, $R_d$, $R_e$ und $R_f$ independently of one another, signify hydrogen, $C_1$–$C_6$-alkyl or phenyl.

If group B signifies linear or branched $C_1$–$C_{12}$-alkylene, $C_2$–$C_{12}$-alkenylene, $C_2$–$C_{12}$-alkynylene, $C_5$–$C_{12}$-cycloalkylene, $C_5$–$C_{12}$-cycloalkenylene, phenylene or phenylene-($C_1$–$C_{12}$)-alkylene substituted by halogen or hydroxy, then at least two functional centres may be present together with the functional group FU, and these can be used for further reactions or for chain extending.

B is most preferably unsubstituted or halogen- or OH-substituted linear or branched $C_1$–$C_{12}$-alkylene.

Examples of alkylene are methylene, ethylene, the various position isomers of propylene, butylene, pentylene, hexylene, heptylene, octylene, nonylene, decylene, undecylene, dodecylene. Examples of substituted alkylenes are 1- or 2-hydroxypropylene, 1-, 2- or 3-hydroxybutylene, the various position isomers of chloropropylene and chlorobutylene. Examples of alkenylene are propenylene, butenylene, pentenylene or hexenylene.

B as cycloalkylene preferably contains 5 to 8, most preferably 5 or 6 ring carbon atoms.

Examples of cycloalkylene are cyclopentylene, cyclohexylene, cycloheptylene, cyclooctylene, cyclodecylene, cycloundecylene and cyclododecylene. Preference is given to cyclopentylene and cyclohexylene, and especially cyclohexylene. Cycloalkylene may be substituted by $C_1$–$C_4$-alkyl, $C_1$–$C_4$-alkoxy, halogen or hydroxy. Examples of such substituents have already been given. Preferred substituents are halogen, OH, methyl and ethyl, as well as methoxy and ethoxy. Examples of substituted cycloalkylene are hydroxycyclohexylene, methyl- and methoxycyclopentylene and -cyclohexylene.

Examples of cycloalkenylene are cyclopentenylene, cyclohexenylene, cycloheptenylene, cyclooctenylene, cyclodecenylene, cycloundecenylene and cyclododecenylene. Preference is given to cyclopentenylene and cyclohexenylene, and especially cyclohexenylene.

B when defined as phenylene or phenylene-($C_1$–$C_{12}$)-alkylene, substituted by $C_1$–$C_4$-alkyl, $C_1$–$C_4$-alkoxy, halogen or hydroxy, preferably contains 1 or 2 substituents. Where phenylene contains 2 or 3 substituents, these may be identical or different. Examples of alkyl and alkoxy substituents have already been given; preferred alkyl and alkoxy substituents for phenylene are methyl, ethyl and methoxy and ethoxy. If the phenylene substituent is halogen, this is preferably —F, —Cl and —Br. Preferred phenylene-$C_1$–$C_{12}$-alkylene are phenylenepropylene, phenyleneethylene or the benzylene group.

Some preferred examples of compounds of formula III are those of formula

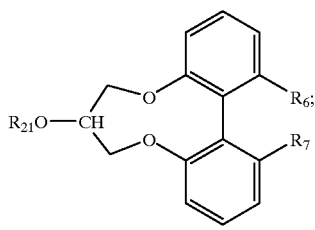

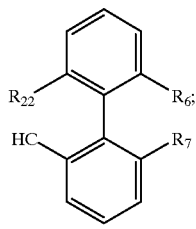

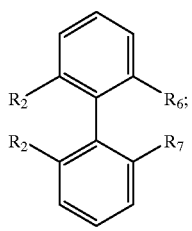

wherein $R_6$ and $R_7$ denote identical or different secondary phosphine groups,
$R_{21}$ is H, $NH_2(CH_2)_3$—, ($C_1$- or $C_2$-alkoxy)$_3Si(CH_2)_3NHC(O)$—,
$R_{22}$ signifies $HOCH_2$—, $H_2NCH_2$—, $NC$—$(CH_2)_2$—$OCH_2$—$H_2N$—$(CH_2)_3$—$OCH_2$— or $H_2N$—$(CH_2)_3$—$HNCH_2$—,
$R_{23}$ is $HO$—$(CH_2)_2$—$O$— or $HO$—$(CH_2)_3$—$O$—, $H_2N$—$(CH_2)_2$—$O$— or $H_2N$—$(CH_2)_3$—$O$—, and $R_{24}$ has the same significance as $R_{23}$ or is methoxy.

A further aspect of the invention is metal complexes of formulae V, Va and Vb of d-8 metals with the compounds of formula III,

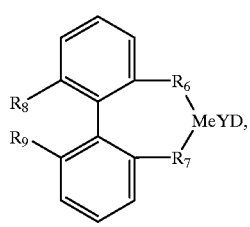

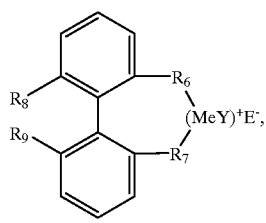

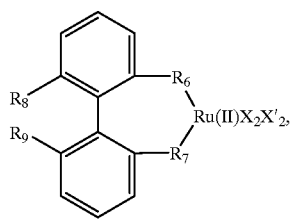

whereby $R_6$, $R_7$, $R_8$ and $R_9$ have the above-mentioned significances and preferences;
Y denotes two monoolefin ligands or one diene ligand;
Me signifies a d-8 metal selected from the group Ir and Rh;
D is —Cl, —Br or —I; and
E is the anion of an oxyacid or complex acid;
$X_2$ and $X_2'$ are identical or different and have the significance of D and E, or $X_2$ and $X_2'$ are allyl or 2-methylallyl, or $X_2$ has the significance of D and E and $X_2'$ is hydride.

Metal complexes in which Y is 1,5-hexadiene, 1,5-cyclooctadiene or norbornadiene are preferred. In the metal complexes according to the invention, D is preferably —Cl, —Br or —I. In the preferred metal complexes, E is $ClO_4^-$, $CF_3SO_3^-$, $CH_3SO_3^-$, $HSO_4^-$, $BF_4^-$, $B(Phenyl)_4^-$, $PF_6^-$, $SbCl_6^-$, $AsF_6^-$ or $SbF_6^-$.

Further ruthenium complexes that may be considered are known in literature and are described for example in U.S. Pat. No. 4,691,037, U.S. Pat No. 4,739,085, U.S. Pat. No. 4,739,084, EP 269395, EP 271310, EP 271311, EP 307168, EP 366390, EP 470756, JP 08081484, JP 08081485, JP 09294932, EP 831099, EP 826694, EP 841343, J. P. Genêt, Arcos Organics Acta, 1 (1995) 4, N. C. Zanetti et al., Organometallics 15 (1996) 860.

The metal complexes of formulae V, Va or Vb are produced by methods known in literature.

The compounds of formulae V, Va and Vb represent catalysts that are already homogeneous and can be used, for example, for hydrogenation of unsaturated organic compounds.

The metal complexes are preferably used for the asymmetric hydrogenation of prochiral compounds with carbon/carbon or carbon/hetero atom multiple bonds, in particular double bonds. Hydrogenations of this type with soluble homogeneous metal complexes are described, for example, in Pure and Appl. Chem., Vol. 68, No. 1, pp. 131–138 (1996).

The compounds of formula III may be covalently bonded to inorganic or organic carriers in a simple manner. A further aspect of the invention is inorganic or organic polymeric carriers, to which diphosphines of formula III

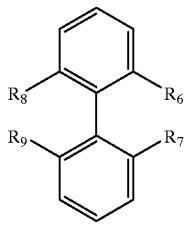

(III)

are bonded. These are characterised in that they are bonded by the functional group FU of radicals $R_8$, $R_9$ or $R_8$ and $R_9$ to the inorganic or polymeric organic carrier, whereby the radicals $R_6$, $R_7$, $R_8$ and $R_9$ have the above-mentioned significances and preferences.

The diphosphines of formula III are preferably bonded to the surface of these carriers. This has the advantage that catalytically active groups of corresponding d-8 metal complexes are also accessible and no inclusion occurs. In this way, during hydrogenation, less catalyst-containing carrier can also be used.

If the compounds of formula III are bonded to inorganic carriers, the functional group FU thereof is advantageously first of all reacted with an alkoxysilylalkyl isocyanate, for example a compound of formula (VI)

$(R_{25})_n(R_{26}O)_{3-n}Si-R_{27}-NCO$ (VI), wherein $R_{27}$ is $C_1$–$C_{12}$-alkylene, $R_{26}$ is $C_1$–$C_{12}$ alkyl, $R_{25}$ is $C_1$–$C_4$-alkyl or $OR_{26}$ and n is 0, 1 or 2; FU in formula III in this case is defined as OH, $NH_2$ or NH—$(C_1$–$C_{12})$-alkyl. Compounds of formulal (IIIa) are obtained,

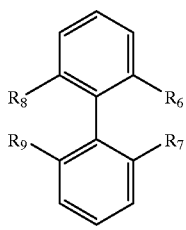

(IIIa)

wherein the group B-FU in radicals $R_8$ and $R_9$ is a radical of formula

—$X_3$—C(O)—NH—$R_{27}$—Si$(R_{25})_n(R_{26}O)_{3-n}$ wherein $X_3$ signifies —O—, —NH— or —N($C_1$–$C_4$-alkyl), and n, $R_{25}$, $R_{26}$ and $R_{27}$ have the abovementioned significances. These compounds are intermediates in the preparation of diphenyldiphosphines bonded to inorganic carriers.

A further aspect of the invention is a solid inorganic carrier, which is characterised in that it has diphosphine ligands of formula IIIa bonded at the surface by one or two silyl groups of the radical of formula —$X_3$—C(O)—NH—$R_{27}$—Si$(R_{25})_n(R_{26}O)_{3-n}$ During this bonding, 1, 2 or 3 alkoxy groups in the silyl radical can be replaced by bonds.

The solid carrier in question may be silicates and semimetal or metal oxides, as well as glass, which preferably exists as powders with average particle sizes of 10 nm to 2000 μm, preferably 10 nm to 1000 μm, most preferably 10 nm to 500 μm. The particles may be both compact and porous. Porous particles preferably have high internal areas, for example 1 to 1200 m², preferably 30 to 600 m². Examples of oxides and silicates are $SiO_2$, $TiO_2$, $ZrO_2$, MgO, NiO, $WO_3$, $Al_2O_3$, $La_2O_3$, silica gels, clays and zeolites. Preferred carriers are silica gels, aluminium oxide, titanium oxide or glass and mixtures thereof. One example of glass as a carrier is "Controlled Pore Glass", which is available commercially.

Preparation of the diphosphine ligands of formula IIIa, which are bonded to inorganic carriers, is described in WO 98/01457.

Owing to the presence of alkoxysilane groups, the compounds of formula IIIa may also be reacted directly to polysiloxanes in a sol-gel process. Reactions of this type have been described for example by U. Deschler et al. in Angew. Chem. 98, (1986), 237–253.

A further aspect of the invention is organic polymeric carriers, to which diphenylphosphines of formula III

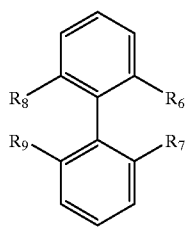

(III)

are bonded by at least one —OH, $NH_2$ group or functional group FU, whereby the radicals $R_6$, $R_7$, $R_8$ und $R_9$ have the above-mentioned significances and preferences. These carriers include both polymers which contain as structural elements the diphenyldiphosphines of formula III, which are bonded by at least one —OH, $NH_2$ group or functional group FU, and polymer particles in which the diphenyldiphosphines of formula III, which are bonded by at least one —OH, $NH_2$ group or functional group FU, are bonded to functional groups at the surface of the particles.

The organic polymeric carriers may be uncrosslinked thermoplastic, crosslinked or structurally crosslinked polymers, which contain functional groups.

The polymers containing functional groups may be either polymers of olefinically unsaturated monomers, for example polyolefins, polyacrylates, polyisoprene, polybutadiene, polystyrene, polyphenylene, polyvinychloride, polyvinylidene chloride or polyallyl compounds, polyaddition compounds, for example polyurethanes or polyethers, or polycondensated products, for example polyesters or polyamides.

The monomers which form the polymer are preferably selected from the group styrene, p-methylstyrene or α-methylstyrene, which contain functional groups. Another preferred group of polymers is formed by monomers that are derived from α,β-unsaturated acids, their esters or amides. Particularly preferred are monomers from the group of acrylates and their $C_1$–$C_4$-alkylesters, methacrylates and their $C_1$–$C_4$-alkylesters, acrylamide and acrylonitrile. An equally preferred group is derived from monomers from the group of acrylates and their $C_1$–$C_4$-alkylesters, methacrylates and their $C_1$–$C_4$-alkylesters, which contain as structural elements, in bonded form, a hydroxyl group or a primary or secondary amine group as functional groups in the ester group.

Bonding of the diphenyldiphosphines of formula III to the polymeric carriers may take place in various ways.

One preferred group of polymerically bonded compounds of formula III is formed in such a way that FU illustrates an olefinically unsaturated radical which is bonded by an ester group OC(O)—$CR_c$=$CR_dR_e$ or an amide group OC($NR_f$)—$CR_c$=$CR_dR_e$ to the bridging group B, wherein $R_c$, $R_d$, $R_e$ und $R_f$ independently of one another, are hydrogen or $C_1$–$C_6$-alkyl, and these are used as comonomers in the radical polymerisation of olefinically unsaturated further monomers. Examples and preferences of further monomers are mentioned above. For the remaining radicals of the compounds of formula III, the above-mentioned significances and preferences apply.

Radical polymerisation is effected in known manner, and a copolymer is obtained which contains diphenyldiphosphine ligands in bonded form.

Another possibility is a polymer-analogous reaction, such as that described by R. Cullen et. al. in J. of Organometallic Chemistry, 333 (1987), 269–280.

Polymer-analogous reactions are possible with polycondensates, such as polyesters, polyamines, which contain directly in a side chain or in the polymer chain a further functional group that is capable of condensation. Examples are hydroxyl-group-containing polyesters or polyethers, which can be reacted with compounds of formula III, whereby in this case the functional group FU preferably signifies —COO($C_1$–$C_{12}$)-alkyl or —COCl.

A further group of preferred polymers that are suitable for polymer-analogous reactions is formed by monomers which contain vinyl alcohol as a homopolymer or vinyl alcohol as a copolymer with vinyl acetate, stearate, benzoate, maleate, vinyl butyral, allyl phthalate, allyl melamine.

Suitable polymers which are equally preferred for polymer-analogous reactions are formed from phenol and a $C_1$–$C_4$-aldehyde, most preferably from phenol and formaldehyde. The polymers are known as phenol-formaldehyde resins, especially as novolaks, and are available commercially.

Another preferred group of polymers which are suitable for polymer-analogous reactions is derived from bisglycidyl ethers and diols. These are hydroxyl-functional polyethers, which are produced for example from bisglycidyl ethers and bisphenol A. These polyepoxides may be built up from diepoxide comonomers with preferably 6 to 40, most preferably 8 to 30 carbon atoms, and diols as comonomers with preferably 2 to 200, most preferably 2 to 50 carbon atoms. One preferred group derived therefrom is formed from monomers, which build up a polymer from cyclic $C_3$–$C_6$-ethers or $C_2$–$C_6$-alkylene glycols with bisglycidyl ethers. The bisglycidyl ethers may be aromatic, aliphatic or cycloaliphatic.

Further preferred polymers with hydroxyl groups as functional groups are polysaccharides. Especially preferred are partial cellulose acetates, propionates or butyrates, partial cellulose ethers, starch, chitin and chitosan.

Further polymers are derived from polymers having reducible groups, for example nitrile groups, ketone groups, carboxylic acid esters and carboxylic acid amides.

Insoluble polymers may also be used in the reaction medium, and these are functionalised at the surface with hydroxyl or amine groups by means of a chemical or physical process. For example, partially unsaturated polymers are provided at their surface with hydroxyl groups by means of oxidation, e.g. with hydrogen peroxide. Another possibility is plasma treatment in, for example, an oxygen atmosphere, nitrogen atmosphere or ammonia atmosphere. The polymers are preferably present as powders. Of these carriers, polystyrene is preferred in particular, and this is subsequently functionalised by known methods with hydroxyl, amino or hydroxymethyl groups.

An especially preferred group is formed by a polymeric organic material with structural elements, in which at least one isocyanate group FU in compounds of formula III is bonded to hydroxyl or amine groups, forming a urethane or urea bond, whereby the hydroxyl or amine groups are bonded directly or in a side chain of the polymer chain. Monomers of formula III with isocyanate groups are obtainable in a simple manner by reacting diisocyanates with amine- or hydroxyl-functional compounds of formula III.

The diphenyldiphosphine radicals of formula III may be present as enantiomer mixtures. The radicals are preferably present in the form of the optically active isomers.

One preferred group of immobilised polymers according to the invention is that in which hydroxy- or aminofunctional polymers are first of all reacted with one isocyanate group of diisocyanates and then the second isocyanate group is reacted with a hydroxy- or amino-functional diphosphine of formula III.

The choice of diisocyanate is in itself not critical. Suitable diisocyantes that are available on a large scale are described for example in Houben Weyl, Makromolekulare Stoffe, volume E 20, pages 1587 to 1583, 1987 edition.

Preference is given to diisocyanates with a bridging group Q, which is selected from the group linear or branched, aliphatic $C_2$–$C_{20}$-alkyl which is unsubstituted or mono- to poly-substituted by $C_1$–$C_6$-alkyl, $C_1$–$C_6$-alkoxy; $C_3$–$C_8$-cycloalkyl or heterocycloalkyl which is unsubstituted or mono- to polysubstituted by $C_1$–$C_6$-alkyl, $C_1$–$C_6$-alkoxy; linear or branched aliphatic $C_2$–$C_{20}$-alkyl unsubstituted or substituted by $C_1$–$C_6$-alkyl, $C_1$–$C_6$-alkoxy and interrupted by $C_3$–$C_8$-cycloalkyl or heterocycloalkyl which is unsubstituted or substituted by $C_1$–$C_6$-alkyl, $C_1$–$C_6$-alkoxy; phenyl, naphthyl, biphenyl or $C_3$–$C_{10}$-heteroaryl either unsubstituted or mono- to polysubstituted by $C_1$–$C_6$-alkyl, $C_1$–$C_6$-alkoxy; linear or branched aliphatic $C_2$–$C_{20}$-alkyl which is unsubstituted or substituted by $C_1$–$C_6$-alkyl, $C_1$–$C_6$-alkoxy and is interrupted by phenyl, naphthyl or $C_3$–$C_{10}$-heteroaryl.

Heterocycloalkyl is e.g. pyrrolidine, piperidine, morpholine, oxazolidine, dioxolan or an isocyanuric acid triester group.

Heteroaryl is for example pyridine, pyrimidine, pyrrole, furan, imidazole, pyrazole or triazine.

Especially preferred diisocyanates are 1,6-bis-[isocyanate]-hexane, 5-isocyanate-3-(isocyanatemethyl)-1,1,3-trimethylcyclohexane, 1,3-bis-[5-isocyanate-1,3,3-trimethyl-phenyl]-2,4-di-oxo -1,3-diazetidine, 3,6-bis-[9-isocyanate-nonyl]-4,5-di-(1-heptenyl)-cyclohexene, bis-[4-isocyanate-cyclohexyl]-methane, trans-1,4-bis-[isocyanate]-cyclohexane, 1,3-bis-[isocyanatemethyl]-benzene, 1,3-bis-[1-isocyanate-1-methyl-ethyl]-benzene, 1,4-bis-[2-cyanate-ethyl]-cyclohexane, 1,3-bis-[isocyanate-methyl]-cyclohexane, 1,4-bis-[1-isocyanate-1-methylethyl]-benzene, bis-[isocyanate]-isododecylbenzene, 1,4-bis-[isocyanate]-benzene, 2,4-bis-[isocyanate]-toluene, 2,6-bis-[isocyanate]-toluene, 2,4-/2,6-bis-[isocyanate]-toluene, 2-ethyl-1,2,3-tris-[3-isocyanate-4-methyl-anilinocarbonyloxy]-propane, N,N'-bis-[3-isocyanate-4-methylphenyl]-urea, 1,4-bis-[3-isocyanate-4-methylphenyl]-2,4-dioxo-1,3-diazetidine, 1,3,5-tris-[3-isocyanate-4-methylphenyl]-2,4,6-trioxohexahydro-1,3,5-triazine, 1,3-bis-[3-isocyanate-4-methylphenyl]-2,4,5-trioxoimidazolidine, bis-[2-isocyanate-phenyl]-methane, (2-isocyanate-phenyl)-(4-isocyanate-phenyl)-methane, bis-[4-isocyanate-phenyl]-methane, 2,4-bis-[4-isocyanate-benzyl]-1-isocyanatbenzene, [4-isocyanate-3-(4-isocyanate-benzyl)-phenyl]-[2-isocyanate-5-(4-isocyanate-benzyl)-phenyl]methane, tris-[4-isocyanate-phenyl]-methane, 1,5-bis-[isocyanate]-naphthaline, or 4,4'-bis[isocyanate]-3,3'-dimethyl-biphenyl.

Particularly preferred diisocyanates are 1,6-bis-[isocyanate]-hexan, 5-isocyanate-3-(isocyanate-methyl)-1,1,3-trimethylcyclohexane, 2,4-bis-[isocyanate]-toluene, 2,6-bis-[isocyanate]-toluene, 2,4-/2,6-bis-[isocyanate]-toluene or bis-[4-isocyanate-phenyl]-methane.

The polymers to be used according to the invention, which contain hydroxyl groups and amine groups, may be uncrosslinked thermoplastic, crosslinked or structurally crosslinked polymers. Examples of hydroxyl-group-containing polymers are those mentioned above.

The polymers to be used according to the invention are known per se, partly commercial or may be produced by known polymerisation processes or by subsequent modification of polymers.

The polymeric organic materials preferably have a molecular weight of 5000 to 5,000,000 daltons, most preferably 50,000 to 1,000,000 daltons.

A preferred sub-group of polymeric organic materials is highly crosslinked macroporous polystyrene or polyacrylate.

Another preferred group of polymers is formed by weakly crosslinked polystyrene. An example thereof is polystyrene crosslinked with 1–5% divinylbenzene.

The particle size of the polymeric organic materials is preferably 10 $\mu$m to 2000 $\mu$m.

The highly crosslinked polymeric organic materials preferably have a specific area of 20 $m^2/g$ to 1000 $m^2/g$, most preferably 50 $m^2/g$ to 500 $m^2g$, determined by the BET method.

Production of the diphenyldiphosphines that are bonded to inorganic or organic carriers may be effected analogously to the processes described in WO 98/01457.

A further aspect of the invention is the d-8 metal complexes of inorganic or organic polymeric carriers, to which diphenyldiphosphines of formula VII, VIIa or VIIb

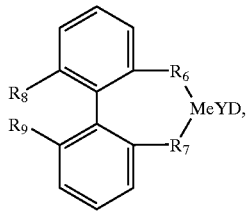

(VII)

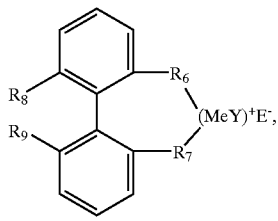

(VIIa)

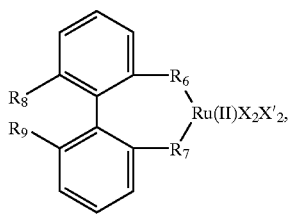

(VIIb)

are bonded by at least one HO—, $H_2N$— group of functional group FU, whereby the radicals $R_6$, $R_7$, $R_8$, $R_9$, Me, E, Y, $X_2$ and $X_2'$ and the carrier have the above-mentioned significances and preferences.

Production of metal complexes with the polymeric carrier may take place by methods known in literature for the production of analogous homogeneous catalysts.

A further aspect of the invention is diphenyldiphosphine ligands of formula III and their d-8 metal complexes of formulae VII, VIIa and VIIb with a molecular weight of preferably less than 5000 daltons, which contain solubility-enhancing or adsorption-facilitating groups bonded to at least one HO—, $H_2N$— or functional group FU, which groups can be separated by extraction with immiscible liquids or by adsorption on a carrier. During extraction, it is preferable to use two immiscible liquids. When using such diphenyldiphosphines and the d-8 metal complexes thereof, there is almost no loss of metal or ligand. Therefore, using these extractable or adsorbable catalysts, large-scale hydrogenation may be carried out especially economically. A preferred group of soluble compounds is those that are soluble in aqueous media.

Suitable immiscible liquids that may be mentioned are, for example, water and organic solvents that are immiscible with water, such as alkanes (for example hexane), chlorinated alkanes (for example methylene chloride, chloroform), aryls (for example toluene, benzene, xylene) or esters (for example ethyl acetate) or organic solvent systems such as fluorinated hydrocarbons and hydrocarbons.

Carriers that are suitable for adsorption are metal oxides, for example silica gel, aluminium oxide, or reversed phase silica gel, polar and apolar polymers and ion exchangers (preferably for ligands with charged radicals).

Suitable solubility-enhancing or adsorption-facilitating radicals may be taken from the publication I. T. Horváth et al. in Science, Vol. 266, pages 72–75 (1994).

Preferred solubility-enhancing radicals for extractable diphenyldiphosphines are, for example, lipophilic radicals which are derived from alkanes having a molecular weight of between 100 and 2000 daltons, or also hydrophilic, optionally charged radicals, which are derived from sugars, or from polymers, for example polyvinyl alcohols, polyacrylic acids, polyethylene glycols, polyvinyl toluene or dendrimers.

Preferred adsorption-facilitating radicals are, for example, lipophilic radicals which are derived from alkanes having a molecular weight of between 100 and 2000 daltons, and also fluoroalkanes.

Further examples of extractable or adsorbable radicals are those that are derived from polyethylene glycols, polyhydroxy hydrocarbons, polyamino hydrocarbons and the ammonium salts thereof, polycarboxyl hydrocarbons and the alkali metal salts thereof, polyhydroxy hydrocarbons or polyamino hydrocarbons, which are reacted with halocarboxylic acids, polyvinyl alcohols, polyaryl acids and the alkali metal salts thereof, higher alkanes and perfluoroalkanes.

The metal complexes according to the invention are eminently suitable as catalysts for the hydrogenation of organic double and triple bonds. Examples are compounds which contain the groups C=C, C=N, C=O, C=C—N or C=C—O (see for example K. E. König, The Applicability of Asymmetric Homogeneous Catalysis, in James D. Morrison (ed.), Asymmetric Synthesis, Vol. 5, Academic Press, 1985). The metal complexes according to the invention are especially suitable for the enantioselective hydrogenation of compounds having prochiral carbon double bonds and carbon/hetero atom double bonds. Examples of such compounds are prochiral alkenes, imines and ketones.

After the reaction, the catalysts according to the invention may be practically completely separated from the reaction mixture in a simple manner, for example by decanting, centrifuging, filtration, ultrafiltration, extraction or adsorption, and reused. One particular advantage of this is that they can be reused several times without any notable losses of activity or selectivity . The catalysts which are functionalised and immobilised according to the invention often have improved optical yields when compared with the previously known diphenylphosphine catalysts.

A further aspect of the invention is therefore the use of the metal complexes of d-8 metals according to the invention as heterogeneous or homogeneous catalysts for the asymmetric hydrogenation of prochiral compounds with carbon double bonds or carbon/hetero atom double bonds. The metal complexes are preferably used for the asymmetric hydrogenation of prochiral compounds with carbon double bonds or carbon/hetero atom double bonds, especially the Ir complexes for the hydrogenation of prochiral ketimines.

A further aspect of the invention is a process for the asymmetric hydrogenation of compounds with carbon double bonds or carbon/hetero atom double bonds, which is characterised in that the compounds are reacted at a temperature of −20 to 80° C. and at a hydrogen pressure of $10^5$ to $2 \times 10^7$ Pa in the presence of catalytic amounts of one or more metal complexes according to the invention.

Catalysts are preferably employed in amounts of 0.0001 to 10 mol %, more preferably 0.001 to 10 mol %, most preferably 0.01 to 5 mol %, based on the compound to be hydrogenated.

Hydrogenation may be carried out continuously or intermittently in various types of reactor. Preference is given to the reactors which allow comparatively favourable blending and good heat removal, e.g. loop reactors. This type of reactor has proved to be particularly effective when using small amounts of catalyst.

The hydrogenated organic compounds that may be produced according to the invention are active substances or intermediates for producing such substances, especially in the field of pharmaceutical and agrochemical production. For example, o,o-dialkylarylketamine derivatives, especially those with alkyl and/or alkoxyalkyl groups, have fungicidal activity, especially herbicidal activity. The derivatives in question may be amine salts, acid amides, e.g. of chloroacetic acid, tertiary amines and ammonium salts (see e.g. EP-A-0 077 755 and EP-A-0 115 470).

The following examples illustrate the invention.
A) Preparation of halomethyidiphenyl diiodides

EXAMPLE A1

(R)-[6-bromomethyl-6'-methyldiphen-2,2'-diyl] bisiodide and (R)-[6,6'-dibromomethyldiphen-2,2'-diyl]bisiodide 3 g of (R)-[6–6'-dimethyidiphen-2,2'-diyl]bisiodide (6.91 mmols), 1.23 g of N-bromosuccinimide (6.91 mmols) and 30 mg of α,α'-azoisobutyronitrile are mixed under argon with 45 ml of $CCl_4$ and heated under reflux for one hour. After adding a spatula tip of α,α'-azobutyronitrile, heating under reflux takes place again for 24 hours. A spatula tip of α,α'-azoisobutyronitrile is again added and heating under reflux takes place for a further 14 hours. The mixture is concentrated on a rotary evaporator and extracted with $H_2O/CH_2Cl_2$. The organic phase is separated, dried ($MgSO_4$), and concentrated on a rotary evaporator. After chromatography on silica gel (hexane→hexane/ethyl acetate (ea)=5/1), 1.98 g of product is isolated as an oil (56%, $3^{rd}$ fraction).

$[\alpha]_D$=+63 ($CH_2Cl_2$, c=0.82).
$^1$H-NMR: 7.96–6.68 (m, 6 arom. H); 4.31 (d, J=10.5; 1H $CH_2Br$); 4.08 (d, J=10.5; 1H $CH_2Br$); 2.17 (s, 1 $CH_3$).

(R)-[6,6'-dibromomethyldiphen-2,2'-diyl]bisiodide is obtained as a by-product in a yield of 9%. $[\alpha]_D$+52,3 (CHCl3, c=1,2) $^1$H-NMR: 7.97–7.2 (m, 6 arom. H); 4.26 (d, J=10.9; 2 CHBr); 4.19 (d, J=10.9, 2 CHBr).
B) Preparation of hydroxymethyldiphenyl bisiodides

EXAMPLE B1

Preparation of R)-[6-hydroxymethyl-6'-methyl-diphen-2,2'-diyl]-bisiodide 14.38 g of the compound according to example A1 (0.028 mols) are dissolved in 350 ml of dioxane and mixed with a KOH solution (18.6 g in 300 ml of $H_2O$). The mixture is heated over night under reflux, whereby a clear solution is obtained. After cooling to room temperature, the mixture is extracted with $CH_2Cl_2$, the organic phase separated, dried ($MgSO_4$) and concentrated on a rotary evaporator. After recrystallisation in cyclohexane, 12.1 g of white crystals are obtained (95.6%). Melting point: 120° C.; $[\alpha]_D$=−25.3 (CHCl$_3$, c=0.73).
$^1$H-NMR: 7.96–7.02 (m, 6 arom. H); 4.35 (d, J=13.8; 1 H $CH_2O$); 4.24 (d, J=13.8; 1 H $CH_2O$); 2.03 (s, 1 $CH_3$); 1.72 (s, 1 HO).
C) Preparation of functional diphenyldiphosphines

EXAMPLE C1

Preparation of

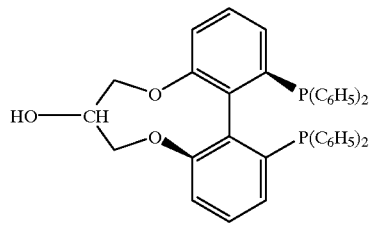

0.47 g of $Cs_2CO_3$ (1.4 mmols) are mixed with 60 ml of absolute $CH_3CN$ and heated under reflux. 100 mg of (R)-6,6'-dihydroxy-diphenyl-2,2'-diphenyldiphosphine (0.18 mmols), dissolved in 5 ml of $CH_3CN$, and 24.7 mg of epibromohydrin (0.18 mmols), dissolved in 5 ml of $CH_3CN$, are slowly added dropwise over the course of 14 hours using a spray pump. Afterwards, a further 8 mg of epibromohydrin (0.06 mmols) are added and heating continues for 2 hours under reflux. The solid residue is filtered and the solution concentrated on a rotary evaporator. After chromatography on silica gel (hexane/ea=4/1), 40 mg of a white solid are obtained (36.3%).

When reacting 100 mg of (R)-6,6'-dihydroxy-diphenyl-2, 2'-diphenyldiphosphine (0.18 mmols) with 39 mg of 1,3-dibromo-2-propanol (0.18 mmols) in the same way as before, 40 mg of the same product are isolated. Melting point: 122° C.; $[\alpha]_D$=−290 (CHCl$_3$, c=1).
$^1$H-NMR: 7.6–6.85 (m, 26 arom. H); 4.48 (d, J=12.9; 1 H $CH_2O$); 4.33 (dd; J=11.2, 5.6; 1 H $CH_2O$); 4.09 (d, J=11.2, 1 H $CH_2O$); 3.98 (dd, J=12.9, 2.6; 1 H $CH_2O$); 3.74 (m; 1 HCOH); 2.04 (d, J=10.3, 1 HO); $^{31}$P{$^1$H}-NMR: −9.6 (s)

EXAMPLE C2

Preparation of

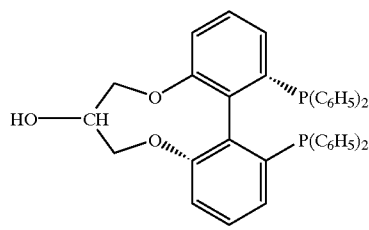

The reaction of 0.4 mg of (S)-6,6'-dihydroxy-diphenyl-2, 2'-diphenyldiphosphine (0.72 mmols) with 98 mg of epibromhydrin in analogous manner to that above yields 144 mg of the title compound (32.7%). Melting point: 122° C.; $[\alpha]_D$=+289 (CHCl$_3$, c=0.8).

¹H-NMR and ³¹P{¹H}-NMR identical to that of compound C1.

EXAMPLE C3

Preparation of

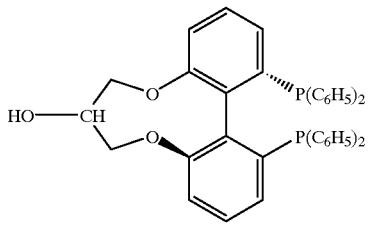

The reaction of 0.1 g of (S,R)-6,6'-dihydroxy-diphenyl-2,2'-diphenyldiphosphine (0,18 mmols) with 24.7 mg of epibromhydrin (0.18 mmols) in the same way as given in example C1 yields 40 mg of product (36.3%). Melting point: 220° C.

¹H-NMR and ³¹P{¹H}-NMR identical to that of compound C1.

EXAMPLE C4

Preparation of

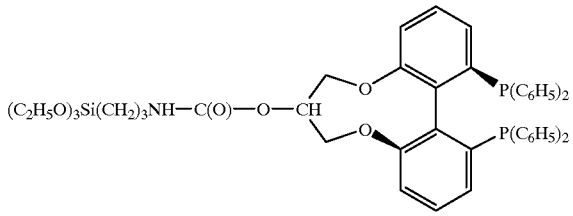

100 mg of compound C1 (0.164 mmols) are dissolved in 6 ml of absolute $CH_2Cl_2$. 122 mg of (3-isocyanatopropyl)-triethoxysilane (0.49 mmol) and 5 ml of dibutyltin-dilaurate are added dropwise, heated under reflux for 16 hours and concentrated on a rotary evaporator. After chromatography on silica gel (hexane/ea=3/1), 95 mg of a white solid are obtained (67.6%). Melting point: 74° C.; $[\alpha]_D$=−137.5 ($CHCl_3$, c=0.8).

¹H-NMR ($CDCl_3$): (2 isomers by reversal of the propyl-triethoxysilane group on nitrogen in a ratio of 6.3 to 1) 7.75–6.65 (m, 26 arom. H); 4.85 (m, 1NH, 1 OCH); 4.7 (br. s, 1 NH)$_{kl}$; 4.45 (br. dd, J=11.6, 3.6; 1 H $CH_2$OPh); 4.3 (br. d, J=11.6; 1 H $CH_2$Ph); 4.1 (br. dd J=11.6, 7.1; 1 H $CH_2$OPh); 3.95 (m, 1 H $CH_2$OPh); 3.85 (q, J=7; 3 $CH_2$O); 3.15 (m, 1 $CH_2$N)$_{gr}$; 2.82 (m, 1 $CH_2$N)$_{kl}$; 1.63 (m, 1 $CH_2CH_2$N)$_{gr}$; 1.50 (m, 1 $CH_2CH_2$N)$_{kl}$; 1.25 (t, J=7; 3 $CH_3$); 0.64 (dd, J=8.3, 7.2; 1 $CH_2$Si)$_{gr}$; 0.55 (m, 1 $CH_2$Si)$_{kl}$.

³¹P{¹H}-NMR: −10.11 (s)$_{gr}$; −9.88 (s)$_{kl}$

EXAMPLE C5

The reaction of 300 mg of compound C2 (0.49 mmols) with 365 mg of (3-isocyanatopropyl)-triethoxysilane (1.47 mmols) according to example C4, yields 260 mg of the (S)-stereoisomer (61.7%). Melting point: 76° C.; $[\alpha]_D$=+138 ($CHCl_3$, c=0.77).

¹H-NMR and ³¹P{¹H}-NMR are identical to compound C4.

EXAMPLE C6

Preparation of (R)-[6-hydroxymethyl-6'-methyl-diphen-2,2'-diyl]-bis-(diphenylphosphine)

a) (R)-[6-(t.-butyl-dimethylsilyloxomethyl)-6'-methyl-biphenyl-2,2'-diyl)-bisiodide 12.17 g of compound B1 (0.027 mols) and 4.44 g of imidazole (0.065 mols) are dissolved in 65 ml of degassed and dried dimethylformamide (DMF). 5.04 g of t.-butyldimethylsilyl chloride (0.033 mols) are added and stirred for 20 hours at 35° C. The solvent is drawn off on a rotary evaporator and the oily residue is extracted with diethylether and water. The organic phase is separated, dried ($MgSO_4$), and concentrated on a rotary evaporator. After chromatography on silica gel (hexane/ea=100/1), 14.58 g of a colourless oil are obtained (95.6%). $[\alpha]_D$=+0.7 ($CHCl_3$, c=1.47).

¹H-NMR: 7.9–7.02 (m, 6 arom H); 4.35 (d, J=14.4; 1 H $CH_2$O); 4.15 (d, J=14.4; 1 H $CH_2$O); 2.02 (s, 1 $CH_3$); 0.91 (s, 3 $CH_3$); 0.03 (s, 1 $CH_3$Si); 0.01 (s, 1 $CH_3$Si).

b) (R)-[6-(t.-butyl-dimethylsilyloxomethyl)-6'-methyl-biphenyl-2,2'-diyl]-bis-(diphenylphosphine)

2.59 g of the above compound a) (4.59 mmols) are dissolved in 50 ml of absolute diethylether and cooled to −78° C. 6.02 ml of lithium butyl solution (1.6 M in hexane, 9.63 mmols) are slowly added dropwise, and the solution is stirred for 5 hours at −78° C. 2.53 g of chlorodiphenylphosphine (11.47 mmols; 2.12 ml) are added dropwise, and the mixture is then heated to room temperature. After 20 hours under reflux, the mixture is concentrated on a rotary evaporator and extracted with $H_2O/CH_2Cl_2$. The organic phase is separated, dried ($MgSO_4$), and concentrated on a rotary evaporator. After chromatography on silica gel (hexane/ea=80/1), 1.62 g of a white solid are isolated (51.8%). Melting point: 97° C.; $[\alpha]_D$=+7.3 ($CHCl_3$, c=0.91).

¹H-NMR: 7.51–7.06 (m, 26 arom. H); 3.75 (d, J=13.3, 1 H $CH_2$O); 3.45 (d, J=13.3, 1 H $CH_2$O); 1.45 (s, 1$CH_3$Ph); 0.81 (s, 3 $CH_3$); −0.18 (s, 1 $CH_3$Si); 0.20 (s, 1 $CH_3$Si).

³¹P{¹H}-NMR: −14.1 (d, J=30); −14.8 (d, J=30).

c) (R)-[6-hydroxymethyl-6'-methyl-diphen-2,2'-diyl]-bis-(diphenylphosphine)

1.522 g of the above compound b) (2.4 mmols) are dissolved in 25 ml of absolute tetrahydrofuran (THF) and mixed with 67 ml of tetrabutylammonium fluoride solution (1 M in THF, 6.7 mmols). The solution is stirred over night (16 hours) and then concentrated in a rotary evaporator. After extraction with water/tert.-butylmethylether, the organic phase is separated, dried ($MgSO_4$) and concentrated on a rotary evaporator. After chromatography on silica gel (hexane/ea=3/1), 1.11 g of a white solid are obtained, which is recrystallised in methanol. A crystalline product is obtained (white needles); yield 0.91 g (71.8%). Melting point: 215° C.; $[\alpha]_D$=−20.4 ($CHCl_3$, c=0.84).

¹H-NMR: 7.40–7.05 (m, 26 arom. H); 3.86 (dd, J=13.7, 9; 1 H $CH_2$O); 3.44 (dd, J=13.7, 4.3; 1 H $CH_2$O); 1.35 (s, 1 $CH_3$); 0.33 (dd, J=9, 4.3; 1 HO).

³¹P{¹H}-NMR: −13.6 (d, J=40.3); −13.9 (d, J=40.3).

EXAMPLE C7

Preparation of (R)-[6-hydroxymethyl-6'-methyl-diphen-2,2'-diyl]-bis-(dicyclohexylphosphine)

a) (R)-[6-(t.-butyl-dimethylsilyloxomethyl)-6'-methyl-biphenyl-2,2'-diyl]-bis-(dicyclohexylphosphine)

1.21 g of compound C6(a) (2.14 mmols) are dissolved in 20 ml of absolute diethylether ($Et_2O$) and cooled to −78° C. 4.5 ml of lithium butyl solution (1.6 M in hexane, 4.5 mmols) are then slowly added dropwise, and the solution is stirred for 2 hours at −78° C. 1.24 g of chlorodicyclohexylphosphine (5.36 mmols) are added dropwise, and the mixture is then heated to room temperature. After 20 hours under reflux, the mixture is extracted with $H_2O/CH_2Cl_2$. The organic phase is separated, dried ($MgSO_4$), and concentrated on a rotary evaporator. After chromatography on silica gel (hexane/ea=100/1), 1.35 g of a colourless oil are isolated (89%). This oil is used further without further purification.

³¹P{¹H}-NMR: −8.5 (d, J=20.8); −9.2 (d, J=20.8).

b) (R)-[6-hydroxymethyl-6'-methyl-diphen-2,2'-diyl]-bis-(dicyclohexylphosphine)

1.348 g of the above compound a) (1.91 mmols) are dissolved in 25 ml of absolute THF and mixed with 5.7 ml of tetrabutylammonium fluoride solution (1 M in THF, 5.7 mmols). The solution is stirred over night (16 hours) and then concentrated in a rotary evaporator. After extraction with water/tert.-butylmethylether, the organic phase is separated, dried (MgSO$_4$) and concentrated on a rotary evaporator. After chromatography on silica gel under argon (hexane/ea=4/1), 0.3 g of a white solid are isolated (26%). M.p.: 213° C.
$^1$H-NMR (CD$_2$Cl$_2$): 7.56–7.21 (m, 6 arom. H); 4.21 (d, J=12.9, 1 H CH$_2$O); 4.10 (dd, J=12.9, 1; 1 H CH$_2$O); 2.15–0.80 (m, 45H: OH+Cy); 1.91 (s, 1 CH$_3$). $^{31}$P{$^1$H}-NMR: −8.9 (s)

EXAMPLE C8

Preparation of (R)-[6-aminomethyl-6'-methyl-diphen-2,2'-diyl]-bis-(diphenylphosphine)

a) (R)-[6-phthalimid-N-yl-methyl-6'-methyl-diphen-2,2'-diyl]-bis-(diphenylphosphine)

0.173 ml (1 mmol) of azodicarboxylic acid diethylester (purity 90%) are added dropwise to a solution of 380 mg (0.67 mmols) of compound C6(c), 352 mg (1.34 mmols) of triphenylphosphine and 128 mg (0.87 mmols) of phthalimide in 15 ml of THF, and the solution stirred over night. The solution is then concentrated on a rotary evaporator, the residue extracted in water/methylene chloride, the organic phase dried with sodium sulphate and concentrated on a rotary evaporator. After purification by chromatography (silica gel Merck 60; eluant=methylene chloride), 130 mg of product are obtained (white powder, yield 28%).
$^1$H-NMR (CDCl$_3$): 7.85–7.6 (m, 4H, phthalimide), 7.5–7.0 (m, 26 arom. H), 4.0 (d, J=14.3, 1 H, CH$_2$—N), 3.8 (d, J=14.3, 1 H, CH$_2$—N), 1.59 (s, 3H, CH$_3$). $^{31}$P{$^1$H}-NMR: −15.4 (s)

b) (R)-[6-aminomethyl-6'-methyl-diphen-2,2'-diyl]-bis-(diphenylphosphine)

128 mg (0.184 mmols) of the above compound a) in 10 ml of ethanol are heated under reflux for 4 hours with 0.15 ml of hydrazine hydrate. The suspension which is obtained upon cooling is filtered, the residue washed with ethyl acetate, and the filtrate concentrated on a rotary evaporator. After purification by chromatography (silica gel Merck 60; eluant =ethanol/triethylamine 250:1), 95 mg of product are obtained (white powder, yield 91%).
$^1$H-NMR (CDCl$_3$): 7.45–7.0 (m, 26 arom. H), 3.05 (d, J=12.3, 1 H, CH$_2$—N), 2.69 (d, J=12.3, 1 H, CH$_2$—N), 1.33 (s, 3H, CH$_3$). $^{31}$P{$^1$H}-NMR: −14.0 (s)

EXAMPLE C9

Preparation of (R)-[6-β-cyanoethyloxymethyl-6'-methyl-diphen-2,2'-diyl]-bis-(diphenylphosphine)

0.107 ml (1.63 mmols) of acrylonitrile and then 0.005 ml of a 40% aqueous KOH solution are added to a solution of 300 mg (0.53 mmols) of compound C6(c) in 3 ml of dioxane, and the reaction solution is subsequently stirred for 24 hours. Then, the solution is concentrated on a rotary evaporator and the product is purified by chromatography (silica gel Merck 60, eluant=methylene chloride). 313 mg of product are obtained (white powder, yield 95%).
$^1$H-NMR (CDCl$_3$): 7.45–7.0 (m, 26 arom. H), 3.68 (d, J=12.5, 1 H, Ph—CH$_2$—O), 3.19 (d, J=12.5, 1 H, Ph—CH$_2$—O), 3.13–2.9 (m, 2H, O—CH$_2$—CH$_2$), 2.3 (t, 2H, CH$_2$—CN), 1.38 (s, 3H, CH$_3$).
$^{31}$P{$^1$H}-NMR: −14.7 (s)

EXAMPLE C10

Preparation of (R)-[6-γ-aminopropyloxymethyl-6'-methyl-diphen-2,2'-diyl]-bis-(diphenylphosphine)

A suspension of 325 mg (0.52 mmols) of compound C9 and 60 mg of LiAlH$_4$ in 5 ml of diethylether is stirred over night. After adding 20 ml of diethylether, the mixture is hydrolysed with ca. 0.5 ml of water and the whole mixture is subsequently dried with sodium sulphate. The solution is concentrated by evaporation and the residue purified by chromatography (silica gel Merck 60, eluant=ethanol/triethylamine 100:1). 157 mg of product are obtained (yield 45%). Compound C6(c) is formed as a by-product.
$^1$H-NMR (CDCl$_3$): 7.45–7.0 (m, 26 arom. H), 3.6 (d, J=12.5, 1 H, Ph—CH$_2$—O), 3.17 (d, J=12.5, 1 H, Ph—CH$_2$—O), 2.96 (m, 2H, O—CH$_2$—CH$_2$), 2.65 (t, J=6.7, 2H, CH$_2$—N), 1.52 (m, 2H, O—CH$_2$—CH$_2$), 1.4 (s, 3H, CH$_3$).

EXAMPLE C11

Preparation of (R)-[6-γ-trimethoxysilylpropylaminocarbonyloxymethyl-6'-methy-diphen -2,2'-diyl]-bis-(diphenylphosphine)

209 mg of compound C6(c) (0.37 mmols) are dissolved in 5 ml of absolute CH$_2$Cl$_2$. To this solution are added dropwise 322 mg of 3-(isocyanatopropyl)-triethoxysilane (0.49 mmols) and 5 ml of dibutyltin dilaurate. The solution is heated under reflux over night and then concentrated in a rotary evaporator. After chromatography on silica gel (hexane/ea=4/1), 260 mg of a colourless oil are obtained (87%). [α]$_D$=21.7 (CHCl$_3$, c=1.12).
$^1$H-NMR (CDCl$_3$): 400.16 MHz): (2 isomers by reversal of the propyl-triethoxysilane group on nitrogen in a ratio of 3.6 to 1) 7.40–7.10 (m, 24 arom. H); 7.06 (m, 2 arom. H); 4.93 (br. s, 1 NH)$_{kl}$; 4.63 (br. t, J=5.7; 1 NH)$_{gr}$; 4.25 (d, J=12.9; 1 H CH$_2$O); 4.13 (q, J=7.3); 3.86 (q, J=7, 3 CH$_2$OSi)$_{kl}$; 3.84 (d, J=7; 1 H CH$_2$O); 3.83 (d, J=7, 3 CH$_2$OSi)$_{gr}$; 3.21 (q, J=6.6; 1 CH$_2$N)$_{kl}$; 3.09 (q, J=6.7; 3 CH$_2$N)$_{gr}$; 1.66 (m, 1CH$_2$CH$_2$N)$_{kl}$; 1.57 (m, 1CH$_2$CH$_2$N)$_{gr}$; 1.43 (s, 1CH$_3$Ph); 1.26 (t, J=7; 3 CH$_3$)$_{kl}$; 1.24 (t, J=7; 3 CH$_3$)$_{gr}$; 0.67 (m, 1 CH$_2$Si)$_{kl}$; 0.60 (m, 1 CH$_2$Si)$_{gr}$. $^{31}$P{$^1$H}-NMR: −13.2 (d, J=34.7); −13.9 (d, J=34.7).

EXAMPLE C12

Preparation of a water-soluble diphosphine of formula

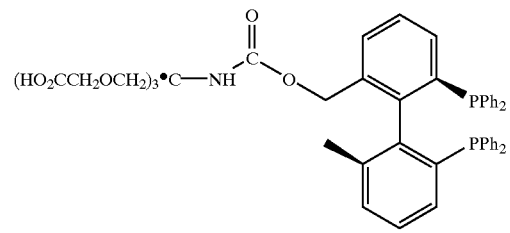

a) A solution of 380 mg (0.9 mmols) of tris-1,2,3-(ethoxycarbonylethyloxymethyl)-2-aminopropane, that has been dried by azeotropic distillation in toluene, in 8.5 ml of absolute toluene is added to 146 mg (0.9 mmols) of 1,1'-carbonyl-diimidazole, and the reaction mixture is stirred for 3 days at room temperature. To this mixture are added first of all a solution of 300 mg (0.53 mmols) of compound C6(c) in 8 ml of absolute toluene and then 20 mg of dibutyltin dilaurate, and the reaction mixture is stirred for 2 days at 100° C. The reaction mixture is then concentrated on a rotary evaporator and purified by chromatography (silica gel Merck 60, eluant: hexane/ethyl acetate 2:1) 415 mg of product are obtained (almost solid oil, yield 80%).

$^1$H-NMR: 7.40–7.0 (m, 26 arom. H); 4.95 (s, 1H, NH), 4.2 (d, J=14, 1 H, CH$_2$O); 4.11 (q, 6H, C$\underline{H}_2$CH$_3$), 3.77 (d, J=14, 1 H CH$_2$O); 3.63 (t, 6H, O—C$\underline{H}_2$CH$_2$), 3.08 (s, 6H, C—CH$_2$—O), 2.5 (t, 6H, O—CH$_2$C$\underline{H}_2$), 1.38 (s, 3H, Ph—CH$_3$), 1.22 (t, 9H, CH$_2$C$\underline{H}_3$).

$^{31}$P{$^1$H}-NMR: −13.6 (d, J=35.7); −14.5 (d, J=35.7).

b) 383 mg (0.377 mmols) of the product are stirred for 18 hours in 10 ml of ethanol, 1 ml of water and 200 mg of potassium hydroxide. Then, the mixture is concentrated on a rotary evaporator and extracted by shaking in 10 ml of methylene chloride and 10 ml of 2n HCl, and the HCl phase is extracted several times with methylene chloride. The methylene phases are combined, washed with 0.2n HCl and then with water, dried with sodium sulphate and concentrated on a rotary evaporator. 333 mg of product are obtained (white solid, yield 95%).

$^1$H-NMR: 7.40–6.9 (m, 26 arom. H); 4.95 (s, 1H, NH), 4.2 (d, J=14, 1 H, CH$_2$O), 3,77 (d, J=14, 1 H CH$_2$O); 3.66 (t, 6H, O—C$\underline{H}_2$CH$_2$), 3.12 (s, 6H, C—CH$_2$—O), 2.51 (t, 6H, O—CH$_2$C$\underline{H}_2$), 1.38 (s, 3H, Ph—CH$_3$).

$^{31}$P{$^1$H}-NMR: −13.7 (d, J=35.2); −14.5 (d, J=35.2).

EXAMPLE C13

Preparation of a Diphosphine of Formula

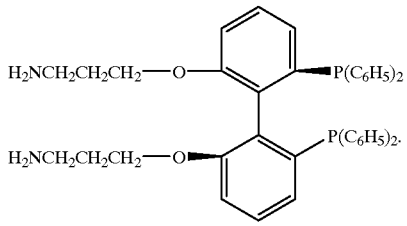

a) A solution of 172 mg (0.31 mmols) of (S)-2,2'-dihydroxy-6,6'-diphenylphosphino-diphenyl in 5 ml of methylene chloride is mixed with 0.3 ml of 30% hydrogen peroxide and the mixture is stirred vigorously over night at room temperature. A white precipitate is formed. This poorly soluble precipitate is filtered, washed with water, ethyl acetate and methylene chloride and dried under a vacuum. The yield is practically quantitative. In $^{31}$P-NMR (suspension in CD$_3$OD/DMSO), the poorly soluble white product has one singlet at δ+33.88 and contains no more educt.

b) 119 mg (0.44 mmols) of N-(3-bromopropyl) phthalimide are added to 104 mg (0.107 mmols) of the accordingly obtained (S)-2,2'-dihydroxy-6,6'-diphenyloxyphosphinodiphenyl and 100 mg of potassium carbonate in 2 ml of N,N-dimethylformamide, and the mixture is stirred over night at 83° C. After cooling, 25 ml of water are added, whereby the product precipitates in pure form practically quantitatively. It is filtered, washed with water and dried under vacuum at 40° C.

$^{31}$P-NMR (CDCl$_3$): +29.9 ppm (s).
$^1$H-NMR (CDCl$_3$) characteristic signals: 3.7 (m, 2H, 2×O—C$\underline{H}$H'—) and 3.33 each (m, 2H, 2×O—CH$\underline{H}$'), 3.33 (t, 4H, 2×CH$_2$—N), 2.5 (m, 4H, 2×C—CH$_2$—C).

The white powder may be reacted to the title compound without further purification, by releasing the amino groups with hydrazine hydrate and reducing the phosphine oxide with trichlorosilane.

D) Preparation of polymers with immobilised diphenyl-diphosphines

EXAMPLE D1

Compound C4 on Silica Gel 2.458 g silica gel (Grace 332; 35–70 mm; Code: 91146025.01) are dried for three hours at 130° C. under a high vacuum and cooled again to room temperature. Then, a solution of 240 mg of compound C4 (2.8 mmols) in 11.5 ml of absolute toluene is added and stirring is carried out over night at 80–90° C. The mixture is cooled to room temperature and the toluene decanted off. The silica gel is then washed five times with 15 ml of degassed methanol and twice with 15 ml of absolute Et$_2$O, and dried over night under a high vacuum at 40° C. Yield: 2.46 g. analysis: 0.26%P corresponding to 0.042 mmols diphosphine/g silica gel.

EXAMPLE D2

Compound C4 on Silica Gel 2.91 g silica gel (Grace 332; 35–70mm; Code: 91146025.01) are dried for three hours at 130° C. under a high vacuum and cooled again to room temperature. Then, a solution of 300 mg of compound C4 (0.35 mmols) in 14.5 ml of absolute toluene and 10 ml of methanesulphonic acid is added. The mixture is stirred over night at 90–110° C. After cooling to room temperature, the toluene is decanted off, and the silica gel is washed five times with 15 ml of degassed methanol and twice with absolute Et$_2$O. The silica gel is then dried over night under a high vacuum at 40° C. Yield: 3.04 g. analysis: P content: 0.39% corresponding to a density of 0.064 mmols diphosphine/g silica gel.

EXAMPLE D3

Compound C3 on Poly-(bisphenol-A-bisglycidylether) (Phenoxy Resin)

0.4 g of polyphenoxy resin with an average molecular weight of 13,000 (1.41 mmols) are dissolved at 40° C. in 10 ml of absolute CH$_2$Cl$_2$. Then, 3.24 ml of 2,4-tolylene-diisocyanate (22.5 mmols) and 20 ml of triethylamine are added. The solution is then stirred under reflux for 3.5 hours. After cooling to room temperature, the polymer is precipitated with 25 ml of absolute pentane and decanted off. The polymer is then washed three times (dissolving in 10 ml of absolute CH$_2$Cl$_2$, precipitating with 25 ml of absolute pentane and filtering). Afterwards, the polymer is almost completely dissolved again in 10 ml of CH$_2$Cl$_2$. To this are added 220 mg of compound C3 (0.36 mmols) and 10 ml of dibutyltin dilaurate. The solution is stirred under reflux for 18 hours and cooled to room temperature. 6 ml of degassed ethanol and 10 ml of dibutyltin are added and stirring is again effected under reflux for 18 hours. After cooling to room temperature, the polymer is precipitated with 50 ml of absolute pentane and 10 ml of absolute Et$_2$O and filtered off. The polymer is washed three times (dissolving in 10 ml of CH$_2$Cl$_2$, precipitating with 25 ml of absolute pentane and 20 ml of absolute Et$_2$O and filtering). The polymer is then dried over night under a high vacuum.

Yield: 510 mg.

Analysis: P: 2.14% corresponding to a density of 0.34 mmols ligand/g polymer.

EXAMPLE D4

Compound C3 with 2,4-tolylene-diisocyanate on Aminomethylated polystyrene 660 mg of aminomethylated polystyrene (NH$_2$: 0.56 mmols/g polymer) (0.37 mmols) are mixed with 25 ml of absolute CH$_2$Cl$_2$. Then, 0.85 ml of 2,4-tolylene-diisocyanate (5.9 mmols) are added dropwise. The mixture is stirred for 3 hours. The solution is filtered and the polymer washed four times with 20 ml of absolute CH$_2$Cl$_2$. The polymer is mixed with 20 ml of CH$_2$Cl$_2$ and then with 225 mg of compound C3 (0.37 mmols), and then 10 ml of dibutyltin dilaurate are added. The mixture is stirred under reflux for 20 hours and then mixed with 8 ml of degassed EtOH, and with a further 10 ml of dibutyltin dilaurate. The mixture is stirred under reflux for a further 18 hours. After cooling to room temperature, the solvent is filtered off and the polymer washed four times with 25 ml of absolute CH$_2$Cl$_2$. The polymer is then dried under a high vacuum. Yield: 754 mg.

Analysis: 0.1% P, corresponding to a density of 0.016 mmols ligand/g polymer.

EXAMPLE D5

Compound C11 on Silica Gel 2.65 g silica gel (Grace 332; 35–70 mm; Code: 91146025.01) are dried for 4.5 hours at 130° C. under a high vacuum and cooled again to room temperature. Then, a solution of 260 mg of compound C11 (0,32 mmols) in 13 ml of absolute toluene and 10 ml of methanesulphonic acid is added. The mixture is stirred over night at 90–105° C. After cooling to room temperature, the toluene is decanted off, and the silica gel is washed five times with 15 ml of degassed MeOH and twice with absolute Et$_2$O. The silica gel is then dried over night under a high vacuum at 40° C. Yield: 2.76 g.

Analysis: P content: 0.39% corresponding to a density of 0.0629 mmols ligand/g silica gel.

EXAMPLE D6

Compound C6(c) with Hexylene-1,6-diisocyanate on Aminomethylated Polystyrene 700 mg of aminomethylated polystyrene (NH$_2$: 0.56 mmols/g polymer) (0.392 mmols) are mixed with 20 ml of absolute CH$_2$Cl$_2$. Then, 2.52 ml of hexamethylene-1,6-diisocyanate (16 mmols) are added dropwise. The mixture is stirred for 2.5 hours. The solution is filtered and the polymer washed four times with 20 ml of absolute CH$_2$Cl$_2$. The polymer is then mixed with 20 ml of CH$_2$Cl$_2$, and 200 mg of compound C6(c) (0.35 mmols) and 10 ml of dibutyltin dilaurate are added. The mixture is stirred under reflux for 22 hours and then mixed with 8 ml of degassed ethanol (EtOH), and 10 ml of dibutyltin dilaurate. The mixture is stirred under reflux for a further 18 hours. After cooling to room temperature, the solvent is filtered off and the polymer washed four times with 25 ml of absolute CH$_2$Cl$_2$. The polymer is then dried under a high vacuum. Yield: 808 mg.

Analysis: 0.3% P corresponding to a density of 0.0484 mmols ligand/g polymer.

E) Hydrogenation

EXAMPLES E1-E14

Hydrogenation of Acetamidocinnamic Acid Methyl Ester

Hydrogenation is carried out as follows: 0.0125 mmols of [Rh(NBD)2]BF4 and 0.015 mmols of polymer are placed under argon in a flask having a magnetic stirrer by repeatedly applying a vacuum and rinsing with argon. Then, 2 ml of degassed methanol are added, the mixture is stirred slowly for 10 minutes (if there are insoluble immobilised ligands, the solution loses its colour and the carrier becomes orange) and 8 ml of a degassed methanolic solution of 2.5 mmols of acetamidocinnamic acid methyl ester are added. Then, without stirring, the argon is replaced by hydrogen (normal pressure) by applying a vacuum and rinsing with hydrogen, and hydrogenation is started by switching on the stirrer. The progress of the reaction can be followed by the consumption of hydrogen (pressure drop in the hydrogen reservoir). The results are listed in table 1.

TABLE 1

| No. | ligand/-polymer ligand | substrate to catalyst | conversion % | reaction time (min.) | optical yield (ee) | remarks |
|---|---|---|---|---|---|---|
| — | Z$_1$ | 200 | 100 | 60 | 29(S) | |
| — | Z$_2$ | 200 | 100 | 50 | 27(R) | |
| E1 | C3 | 200 | 100 | 55 | 41(S) | |
| E2 | C4 | 200 | 100 | 60 | 39(S) | |
| E3 | C6(C) | 200 | 100 | 70 | 38(R) | |
| E4 | C11 | 200 | 100 | 90 | 36(R) | |
| E5 | D1 | 200 | 100 | 70 | 44(S) | |
| E6 | D1 | 200 | 100 | 120 | 43(S) | reused |
| E7 | D1 | 1000 | 93 | 900 | 39(S) | |
| E8 | D2 | 200 | 100 | 60 | 45(S) | |
| E9 | D3 | 200 | 98 | 90 | 48(R) | catalyst insoluble |
| E10 | D3 | 200 | 42 | 125 | 46(R) | reused |
| E11 | D3 | 200 | 100 | 60 | 41(S) | in methanol/THF with methanesulphonic acid |
| E12 | D4 | 200 | 100 | 80 | 40(R) | |
| E13 | D4 | 200 | 100 | 110 | 40(R) | reused |
| E14 | D5 | 400 | 50 | 840 | 39(R) | in methanol/THF with methanesulphonic acid |

Z$_1$: (S)-6,6'-dimethoxy-diphen-2,2'-yl-bis-(diphenylphosphine)
Z$_2$: (S)-6,6'-dimethyl-diphen-2,2'-yl-bis-(diphenylphosphine)

EXAMPLES E15–E34

Hydrogenation of Phenylglyoxalic Acid Methyl Ester to S-mandelic Acid Methyl Ester Hydrogenation is carried out as follows: 2 ml of degassed acetone are added under argon to 0.013 mmols of (cyclooctadiene)Ru(2-methylallyl)$_2$ and 0.0143 mmols of immobilised ligand D1. Then, the indicated amounts of HBr or methanesulphonic acid or LiBr are added, stirring is effected for 30 minutes, and finally the acetone is drawn off under vacuum. Then, a degassed solution of 5 mmols of phenylglyoxalic acid methyl ester in 5 ml of methanol is added, the reaction mixture is transferred by a cannula under a countercurrent of argon into a 50 ml autoclave, and hydrogenated at 80 bars hydrogen pressure at 40° C.

The immobilised catalyst is reused several times. Separation takes place each time by centrifuging. The results are listed in table 2. In examples E24–34, 4.6 equivalents of LiBr/Ru are additionally used. The acid addition is given in equivalents per Ru. MS signifies methanesulphonic acid.

TABLE 2

| No. | acid addition | LiBr addition | sub-strate to catalyst | con-version (%) | ee (%) | reaction time (min.) | remarks |
|---|---|---|---|---|---|---|---|
| E15 | 3.4 HBr | — | 384 | 98.5 | 86.1 | 1320 | fresh catalyst |
| E16 | — | — | 384 | 93.6 | 75.7 | 1100 | 1st reuse |
| E17 | 7.4 HBr | — | 384 | 99 | 87.1 | 1080 | fresh catalyst |
| E18 | 7.4 HBr | — | 384 | 99 | 89.1 | 1100 | 1st reuse |
| E19 | 7.4 HBr | — | 384 | 99 | 88.7 | 960 | 2nd reuse |
| E20 | 7.4 HBr | — | 384 | 97 | 88.6 | 960 | 3rd reuse |
| E21 | 7.4 HBr | — | 384 | 99 | 90 | 3780 | 4th reuse |
| E22 | 4.5 HBr | — | 1000 | 47 | 79 | 960 | fresh catalyst |
| E23 | 4.5 HBr | — | 1000 | 65 | 81.8 | 1200 | 1st reuse |
| E24 | 2.3 MS | 4.6 LiBr | 384 | 79 | 81.9 | 870 | fresh catalyst |
| E25 | 2.3 MS | 4.6 LiBr | 384 | 95 | 86.7 | 1050 | 1st reuse |
| E26 | 4.6 MS | 4.6 LiBr | 384 | 99 | 90.7 | 960 | 2nd reuse |
| E27 | 2.3 MS | 4.6 LiBr | 384 | 99 | 86.7 | 960 | 3rd reuse |
| E28 | 4.6 MS | 4.6 LiBr | 384 | 99 | 87.7 | 900 | 4th reuse |
| E29 | 4.6 MS | 4.6 LiBr | 1000 | 02 | 85.8 | 1440 | 5th reuse |
| E30 | 4.6 MS | 4.6 LiBr | 384 | 97 | 86.3 | 1200 | 6th reuse |
| E31 | 4.6 MS | 4.6 LiBr | 384 | 97 | 87.1 | 1140 | 7th reuse |
| E32 | 4.6 MS | 4.6 LiBr | 1000 | 76 | 83.7 | 1200 | 8th reuse |
| E33 | 4.6 MS | 4.6 LiBr | 1000 | 57 | 81.3 | 900 | 9th reuse |
| E34 | 4.6 MS | 4.6 LiBr | 1000 | 35 | 74.1 | 1200 | 10th reuse |

What is claimed is:
1. Compounds of formula III,

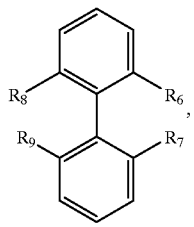

(III)

wherein
R$_6$ and R$_7$ signify identical or different secondary phosphino,
R$_8$ is —CH$_2$—O—B—(FU)$_p$, —CH$_2$—NR'—B—(FU)$_p$,
R$_9$ has the same significance as R$_8$ or is C$_1$–C4-alkyl or C$_1$–C$_4$-alkoxy, or
R$_8$ and R$_9$ together signify (FU)$_p$—B—OCH(CH$_2$—O—)$_2$ or (FU)$_p$—B—R'NCH(CH$_2$—O—)$_2$,
R' is H or C$_1$–C$_4$ alkyl;
B is a bridging group,
FU is a functional group which can covalently bond to an organic or inorganic carrier, p is a number from 1 to 6, and
NH$_2$ groups are present as such or as masked isocyanate groups.
2. Compounds according to claim 1, in which the secondary phosphino group corresponds to formula —PR$_{10}$R$_{11}$, wherein R$_{10}$ and R$_{11}$, independently of one another, are C$_1$–C$_{12}$-alkyl, C$_5$–C$_{12}$-cycloalkyl, phenyl, C$_5$–C$_{12}$-cycloalkyl substituted by C$_1$–C$_4$-alkyl or C$_1$–C$_4$-alkoxy, or phenyl mono- to trisubstituted by C$_1$–C$_4$-alkyl, C$_1$–C$_4$-alkoxy, —SiR$_{12}$R$_{13}$R$_{14}$, halogen, —SO$_3$M, —CO$_2$M, —PO$_3$M, —NR$_{15}$R$_{16}$, —[$^+$NR$_{15}$R$_{16}$R$_{17}$]X$^-$ or C$_1$–C$_5$-fluoroalkyl; R$_{10}$ and R$_{11}$ together are tetra- or pentamethylene either unsubstituted or mono- to trisubstituted by C$_1$–C$_4$-alkyl, C$_1$–C$_4$-alkoxy, —SiR$_{12}$R$_{13}$R$_{14}$, halogen, —SO$_3$M, —CO$_2$M, —PO$_3$M, —NR$_{15}$R$_{16}$, —[$^+$NR$_{15}$R$_{16}$R$_{17}$]X$^-$ or C$_1$–C$_5$-fluoroalkyl, or the group —PR$_{10}$R$_{11}$ represents a radical of formulae

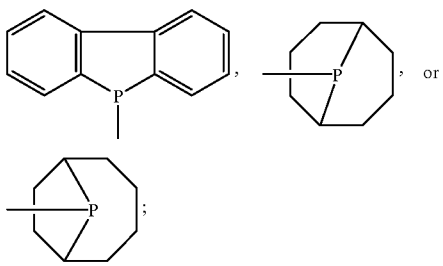

and R$_{12}$, R$_{13}$ and R$_{14}$ independently of one another, are C$_1$–C$_{12}$-alkyl or phenyl R$_{15}$ and R$_{16}$, independently of one another, are H, C$_1$–C$_{12}$-alkyl or phenyl, or R$_{15}$ and R$_{16}$ together are tetramethylene, pentamethylene or 3-oxa-1,5-pentylene;
R$_{17}$ is H or C$_1$–C$_4$-alkyl;
M is H or an alkali metal;
X is the anion of a monobasic acid;
halogen is fluorine, chlorine, bromine or iodine.
3. Diphenyldiphosphine ligands of formula III according to claim 1, which contain groups enhancing solubility in a liquid or groups facilitating adsorption on a carrier bonded to at least one functional group FU, and which have a molecular weight of less than 5000 daltons, and which can be separated from a liquid by extraction with immiscible liquids or by adsorption on a carrier.
4. A compound according to claim 2, in which R$_{10}$ and R$_{11}$ are linear or branched alkyl, which contain 1 to 8 carbon atoms.
5. A compound according to claim 4, in which R$_{10}$ and R$_{11}$ are methyl, ethyl, n- or isopropyl, n-, iso- or tert-butyl.
6. A compound according to claim 4, in which R$_{10}$ and R$_{11}$ are cycloalkyl containing 5 to 8 ring carbon atoms.
7. A compound according to claim 2, in which R$_{10}$ and R$_{11}$ are cyclopentyl, cyclohexyl, cycloheptyl, cyclooctyl, cyclodecyl or cyclododecyl.
8. A compound according to claim 2, in which R$_{10}$ and R$_{11}$ are phenyl substituted by 1 or 2 substituents.
9. A compound according to claim 2, in which R$_{10}$ and R$_{11}$ are phenyl, 2methyl-phenyl, 3-methyl-phenyl, 4-methyl-phenyl, 2- or 4ethyl-phenyl, 2- or 4-isopropyl-phenyl, 2- or 4-tert-butyl-phenyl, 2-methoxy-phenyl, 3-methoxy-phenyl, 4-methoxy-phenyl, 2- or 4-ethoxy-phenyl, 4-trimethylsilyl-phenyl, 2- or 4or 4-fluoro-phenyl, 2,4-difluoro-phenyl, 2- or 4-chloro-phenyl, 2, 4-dichloro-phenyl, 2,4-dimethyl-phenyl, 3,5-dimethyl-phenyl, 2-methoxy-4-methyl-phenyl, 3,5-dimethyl-4-methoxy-phenyl, 3,5-dimethyl-4-(dimethylamino)-phenyl, 2- or 4-amino-phenyl, 2- or 4-methylamino-phenyl, 2- or 4-(dimethylamino)-phenyl, 2- or 4SO$_3$H-phenyl, 2- or 4-SO$_3$Na-phenyl, 2-or 4-[$^+$NH$_3$Cl$^{31}$]-phenyl, 3,4,5-trimethylphen-1-yl, 2,4,6-trimethylphen-1-yl, 4-trifluoromethyl-phenyl or 3,5-di-(trifluoromethyl)-phenyl.

10. A compound according to claim 2, in which X$^-$ is Cl$^{31}$, Br$^-$ or the anion of a carboxylic acid or sulfonic acid.

* * * * *